US012682988B2

(12) United States Patent
Choi et al.

(10) Patent No.: US 12,682,988 B2
(45) Date of Patent: Jul. 14, 2026

(54) METHOD, APPARATUS, AND COMPUTER PROGRAM FOR AUTOMATICALLY GENERATING STANDARDIZED RESEARCH RECORD DATA FOR TRAINING ARTIFICIAL INTELLIGENCE MODEL

(71) Applicant: ANT INC., Daejeon (KR)

(72) Inventors: Jong Yun Choi, Daejeon (KR); Sukjoo Hong, Daejeon (KR); Sangyoon Lee, Seoul (KR)

(73) Assignee: ANT INC., Daejeon (KR)

( * ) Notice: Subject to any disclaimer, the term of this patent is extended or adjusted under 35 U.S.C. 154(b) by 501 days.

(21) Appl. No.: 18/320,800

(22) Filed: May 19, 2023

(65) Prior Publication Data

US 2023/0290445 A1 Sep. 14, 2023

Related U.S. Application Data

(63) Continuation of application No. PCT/KR2021/017196, filed on Nov. 22, 2021.

(30) Foreign Application Priority Data

| Nov. 20, 2020 | (KR) | ........................ | 10-2020-0157187 |
| Feb. 9, 2021 | (KR) | ........................ | 10-2021-0018205 |

(51) Int. Cl.
*G16C 20/50* (2019.01)
*G06F 40/284* (2020.01)
(Continued)

(52) U.S. Cl.
CPC .......... *G16C 20/50* (2019.02); *G06F 40/284* (2020.01); *G06F 40/40* (2020.01); *G16C 20/70* (2019.02); *G16C 60/00* (2019.02)

(58) Field of Classification Search
CPC ..... G06F 40/20; G06F 16/9035; G16C 20/50; G16C 60/00
See application file for complete search history.

(56) References Cited

U.S. PATENT DOCUMENTS

| 2019/0278880 A1 | 9/2019 | Ma et al. |
| 2019/0378029 A1 | 12/2019 | Aykol et al. |
| | (Continued) | |

FOREIGN PATENT DOCUMENTS

| JP | 2001-505223 A | 4/2001 |
| JP | 2012-078650 A | 4/2012 |
| | (Continued) | |

OTHER PUBLICATIONS

L. Himanen et al., "Data-Driven Materials Science: Status, Challenges and Perspectives", Adv. Sci., vol. 6, 1900808, Sep. 1, 2019, pp. 1-23.
(Continued)

*Primary Examiner* — Lam S Nguyen
(74) *Attorney, Agent, or Firm* — Studebaker Brackett PLLC

(57) ABSTRACT

Provided are a method, apparatus, and computer program for automatically generating standardized research record data for training an artificial intelligence model. The method for automatically generating standardized research record data for training an artificial intelligence model, according to various embodiments of the present invention, is performed by a computing apparatus and comprises the steps of: acquiring research record information regarding an experiment; processing the acquired research record information on the basis of prestored data related to the experiment; and generating standardized research record data by using the processed research record information.

10 Claims, 20 Drawing Sheets

(51) Int. Cl.
    *G06F 40/40*         (2020.01)
    *G16C 20/70*         (2019.01)
    *G16C 60/00*         (2019.01)

(56)         References Cited

U.S. PATENT DOCUMENTS

| 2020/0097838 A1* | 3/2020 | Tsuchiya | G06F 16/9035 |
| 2021/0109958 A1* | 4/2021 | Behtash | G06F 40/20 |

FOREIGN PATENT DOCUMENTS

| JP | 2019-185506 A | 10/2019 |
| JP | 2020-052602 A | 4/2020 |
| JP | 2020-529057 A | 10/2020 |
| KR | 10-2011-0054926 A | 5/2011 |
| KR | 10-2014-0121061 A | 10/2014 |
| KR | 10-2020-0003407 A | 1/2020 |

OTHER PUBLICATIONS

P. Ristoski et al., "Expert-in-the-loop AI for Polymer Discovery", CIKM '20, Oct. 19, 2020, Virtual Event, Ireland, pp. 2701-2708.

C. Empel et al., "Artificial-Intelligence-Driven Organic Synthesis-En Route towards Autonomous Synthesis?", Angew. Chem. Int. Ed., vol. 58, Oct. 22, 2019, pp. 17114-17116.

O. Kononova et al., "Text-mined dataset of inorganic materials synthesis recipes", Scientific Data, vol. 6, 203, Oct. 15, 2019, pp. 1-11.

S. P. Ong, "Accelerating materials science with high-throughput computations and machine learning", Computational Materials Science, vol. 161, Feb. 1, 2019, pp. 143-150.

An Office Action mailed by the Korean Intellectual Property Office on Feb. 7, 2024, which corresponds to Korean Patent Application No. 10-2022-0187421 and is related to U.S. Appl. No. 18/320,800.

An Office Action mailed by the Korean Intellectual Property Office on Feb. 16, 2024, which corresponds to Korean Patent Application No. 10-2022-0187422 and is related to U.S. Appl. No. 18/320,800.

International Search Report issued in PCT/KR2021/017196; mailed Feb. 28, 2022.

King, Ross D. et al.; "On the formalization and reuse of scientific research"; J. R. Soc. Interface; 2011; vol. 8; pp. 1440-1448.

Roh, Yuji et al.; "A Survey on Data Collection for Machine Learning"; arXiv:1811.030402v2; 2019; pp. 1-20.

Soedarmadji, Edwin et al.; "Tracking materials science data lineage to manage millions of materials experiments and analyses"; Npj Computational Materials; vol. 5:79; 2019; pp. 1-9.

Li, Jiali et al.; "AI Applications through the Whole Life Cycle of Material Discovery"; Matter, vol. 3; Aug. 5, 2020; pp. 393-432.

Swain et al., "ChemDataExtractor: A Toolkit for Automated Extraction of Chemical Information from the Scientific Literature", Journal of Chemical Information and Modeling [online], Oct. 2016, vol. 56, No. 10, 1 page.

Krallinger et al., "CHEMDNER: The drugs and chemical names extraction challenge", Journal of Cheminformatics [online], Jan. 2015, vol. 7, Supplement 1, 40 pages.

Krallinger et al., "Information Retrieval and Text Mining Technologies for Chemistry", Chemical Reviews [online], Jun. 2017, vol. 117, No. 12, 1 page.

An Office Action mailed by the Japanese Patent Office on May 2, 2024, which corresponds to Japanese Patent Application No. 2023-528695 and is related to U.S. Appl. No. 18/320,800; with English language translation.

\* cited by examiner

BUILD DB BY COLLECTING EXPERIMENT AND
RESEARCH-RELATED WORDS SELECTED FROM
BUNT PAPERS AND PATENTS

Vocabulary,
(solution, AgNO3, mL, mM,
add, mixture, trisodium
citrate, PSSS, mg/L,
NaBH4, water, mL/min,
stir, ···)

Tag,
(material, chemical,
formula, cas# product #,
smiles code, dna, animal,
instrument, unit, process,
device fabrication,
synthesis, PCR, treatment,
analysis, measure, ···)

$\pi$ : ORDER OF NODE IN GRAPH $S_n^\pi$ : GRAPH IN CASE OF SEQUENCE N $S_{i,j}^\pi$ : EDGE OF NODES I AND J
(1 INDICATES CONNECTION)

FIG. 9

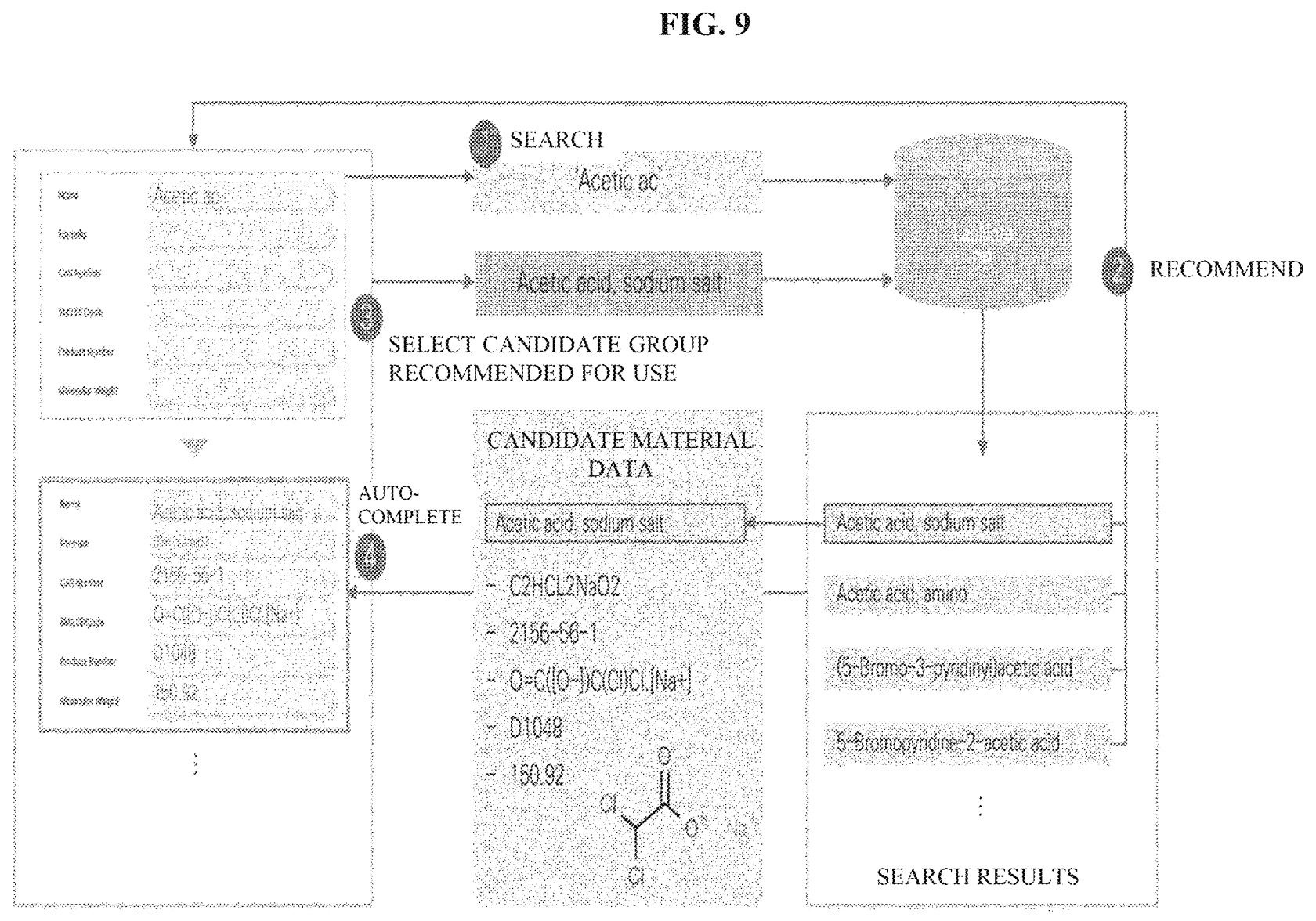

RECOMMEND

SEARCH

'Acetic ac'

Acetic acid, sodium salt

SELECT CANDIDATE GROUP
RECOMMENDED FOR USE

CANDIDATE MATERIAL
DATA

Acetic acid, sodium salt

– C2HCl2NaO2
– 2156-56-1
– O=C([O-])C(Cl)Cl.[Na+]
– D1048
– 150.92

AUTO-
COMPLETE

Acetic acid, sodium salt

Acetic acid, amino (6-Bromo-3-pyridinyl)acetic acid

5-Bromopyridine-2-acetic acid

. . .

SEARCH RESULTS

FIG. 10

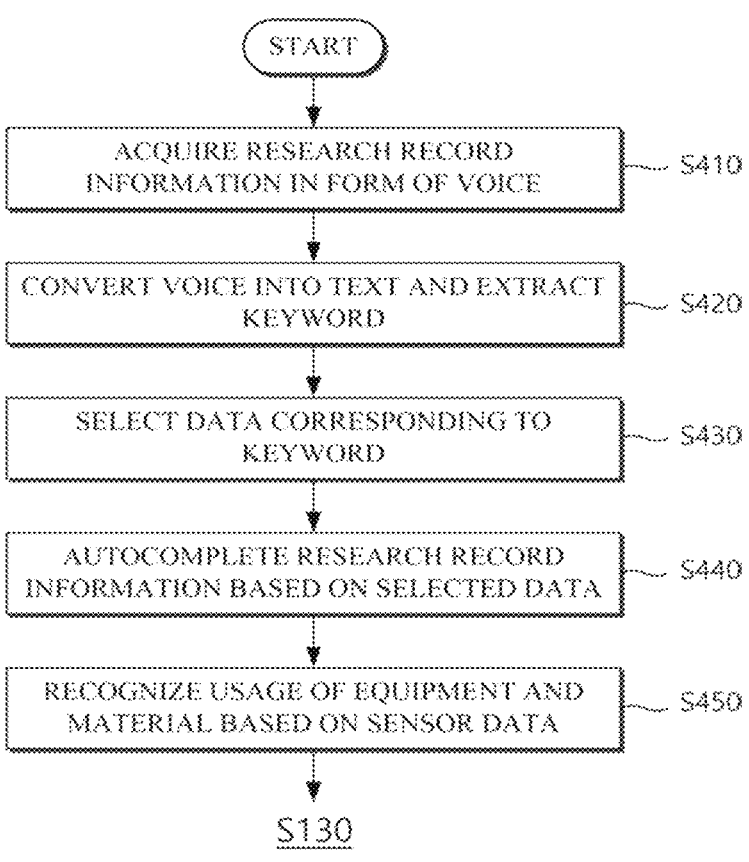

START

ACQUIRE RESEARCH RECORD INFORMATION IN FORM OF VOICE — S410

CONVERT VOICE INTO TEXT AND EXTRACT KEYWORD — S420

SELECT DATA CORRESPONDING TO KEYWORD — S430

AUTOCOMPLETE RESEARCH RECORD INFORMATION BASED ON SELECTED DATA — S440

RECOGNIZE USAGE OF EQUIPMENT AND MATERIAL BASED ON SENSOR DATA — S450

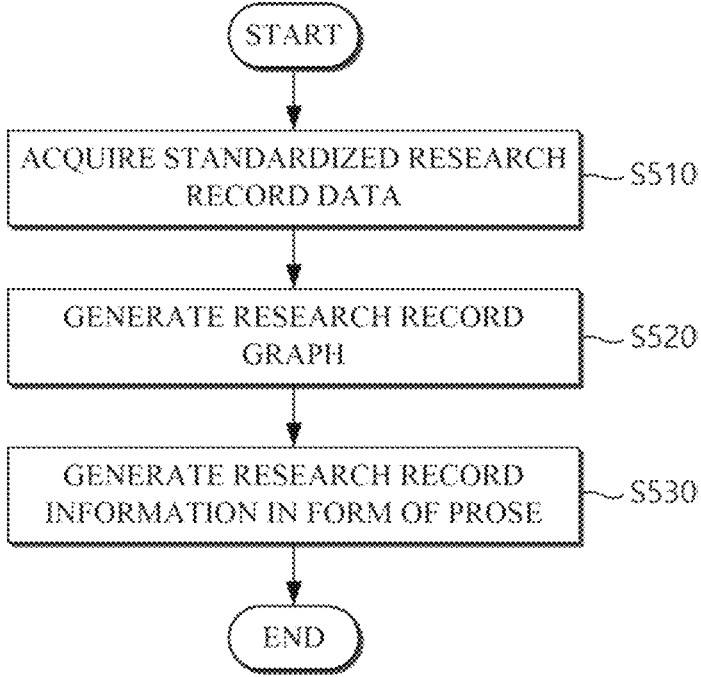

START

ACQUIRE STANDARDIZED RESEARCH RECORD DATA — S510

GENERATE RESEARCH RECORD GRAPH — S520

GENERATE RESEARCH RECORD INFORMATION IN FORM OF PROSE — S530

END

Figure 19:
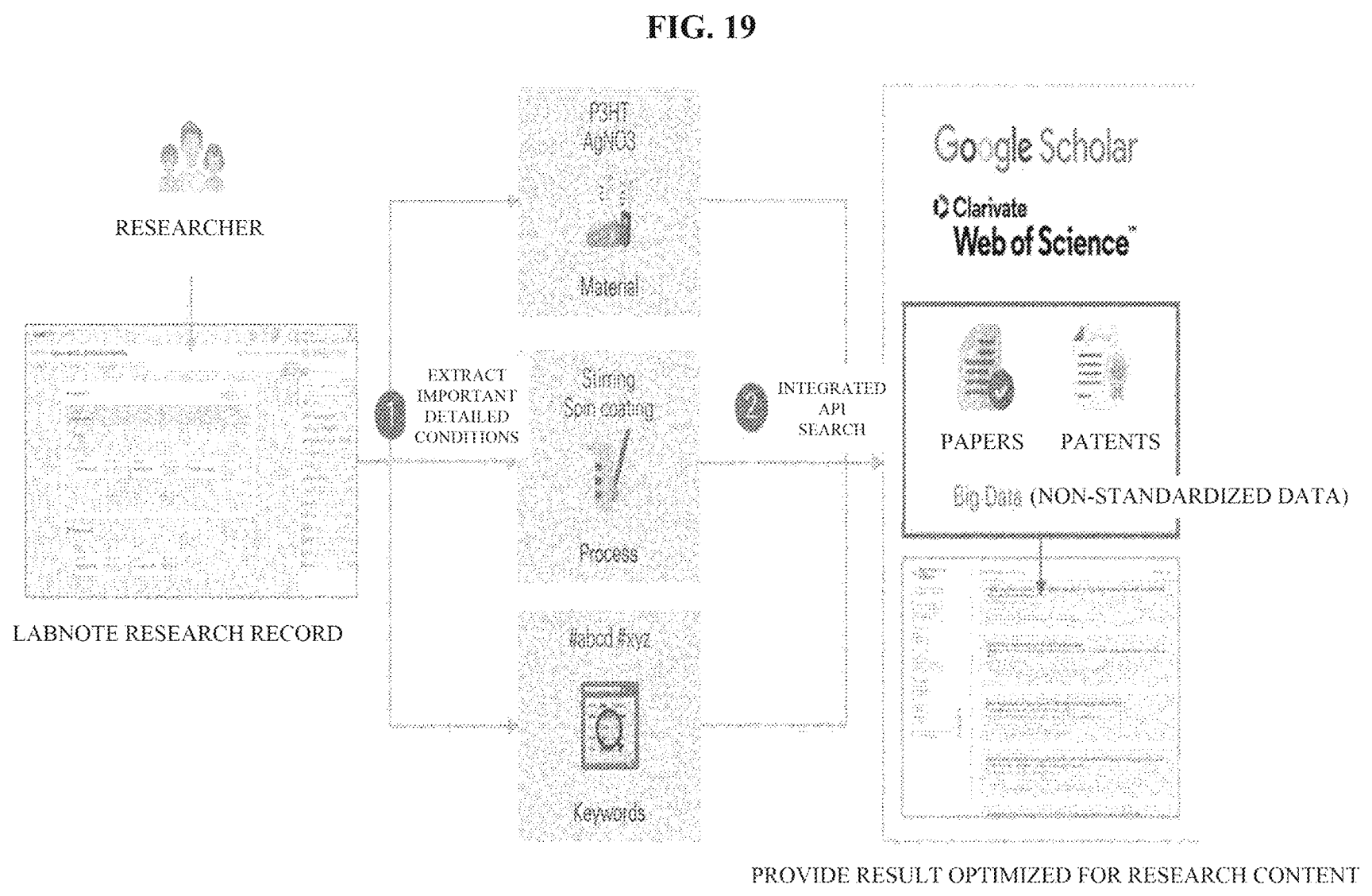

PROVIDE RESULT OPTIMIZED FOR RESEARCH CONTENT

Google Scholar

Clarivate Web of Science™

PAPERS   PATENTS

Big Data (NON-STANDARDIZED DATA)

INTEGRATED API SEARCH

Material

Process

Keywords

EXTRACT IMPORTANT DETAILED CONDITIONS

RESEARCHER

LABNOTE RESEARCH RECORD

METHOD, APPARATUS, AND COMPUTER PROGRAM FOR AUTOMATICALLY GENERATING STANDARDIZED RESEARCH RECORD DATA FOR TRAINING ARTIFICIAL INTELLIGENCE MODEL

CROSS-REFERENCE TO RELATED APPLICATION

This application is a continuation of PCT/KR2021/017196, filed on Nov. 22, 2021, which claims priority to and the benefit of Korean Patent Application Nos. 10-2021-0018205, filed on Feb. 9, 2021 and 10-2020-0157187, filed on Nov. 20, 2020, the disclosure of which is incorporated herein by reference in its entirety.

TECHNICAL FIELD

The present invention relates to a method, a device, and a computer program for automatically generating standardized research record data for training an artificial intelligence model.

BACKGROUND ART

In general, bio and nano research is conducted through the steps of synthesizing substances and materials, checking a structure and composition, measuring several properties for determining an application possibility, and commercializing applications.

Here, when the structure and composition of an optimized material are not drawn in the step of checking a structure and composition or a desired property is not specified in the step of measuring several properties for determining an application possibility, the process should be performed again from the step of synthesizing substances and materials. Since it is necessary to repeat the step of synthesizing substances and materials to find an optimized material, it takes a minimum of several months to a maximum of several years to find an optimized material, and high costs are paid for synthesis, examination, etc., which are problematic.

Meanwhile, to solve such conventional problems, methods of using an artificial intelligence model trained with various information and data related to bio and nano research are being proposed.

To use an artificial intelligence model, it is necessary to generate research record data as data for training the artificial intelligence model. Such research record data used as training data is written by researchers or experimenters recording experiment information in detail. Accordingly, there are various problems such as the hassle of repetitive and similar records and the like, missing of important requirements for an experiment, necessity for data reprocessing upon data use, difficulty in analysis and management due to generation of massive data, etc.

DISCLOSURE

Technical Problem

The present invention is directed to providing a method, a device, and a computer program for automatically generating standardized research record data for training an artificial intelligence model which increase the convenience of recording, greatly improve the accuracy of records, and facilitate analysis, sharing, and management of research processes and results by processing non-standardized research record information and automatically generating standardized research record data and also can assist in developing synthetic materials more conveniently and quickly by providing a synthetic material development process for drawing information on synthetic materials which satisfy specific conditions, and guide information for synthesizing the synthetic materials through an artificial intelligence model which is trained using research record data standardized according to the above method as training data.

Objectives to be achieved by the present invention are not limited to that described above, and other objectives not have been described above can be clearly understood by those of ordinary skill in the art from the following description.

Technical Solution

One aspect of the present invention provides a method of automatically generating standardized research record data for training an artificial intelligence model, the method being performed by a computing device and including acquiring research record information of an experiment, processing the acquired research record information on the basis of prestored experiment-related data, and generating standardized research record data using the processed research record information.

The processing of the acquired research record information may include, when research record information in a form of prose including one or more text sentences is acquired, tokenizing each of a plurality of words included in the acquired research record information in the form of prose and labeling each of the plurality of tokenized words with attribute information to generate processed research record information, and the generating of the standardized research record data may include generating a research record graph using the processed research record information and generating the standardized research record data using the generated research record graph.

The generating of the standardized research record data using the generated research record graph may include generating an adjacency matrix using the plurality of words labeled with the attribute information as input data for a pretrained first model and generating the research record graph which includes nodes each corresponding to the plurality of words and edges connecting the plurality of words, using the generated adjacency matrix. The pretrained first model may be a domain language learning model based on a transformer structure including a plurality of encoders.

The processing of the acquired research record information may include, when one or more keywords which include at least one of a keyword relating to an experimental material, a keyword relating to a research and experiment process, and a keyword relating to a research result, are input by a user through a user interface (UI), selecting experiment-related data corresponding to the one or more input keywords on the basis of the prestored experiment-related data and autocompleting research record information corresponding to the one or more input keywords using the selected experiment-related data.

The autocompleting of the research record information corresponding to the one or more input keywords may include, when a plurality of pieces of experiment-related data correspond to the one or more input keywords, providing one or more pieces of experiment-related data to the user as recommendation data from among a plurality of pieces of experiment-related data on the basis of the user's search history and, when the provided recommendation data is selected by the user, autocompleting the research record information corresponding to the one or more input keywords using the selected recommendation information.

The processing of the acquired research record information may include, when research record information in a form of voice is input by a user through a UI, performing natural language processing (NLP) on the input research record information in the form of voice to convert the input research record information in the form of voice into research record information in a form of text, analyzing the converted research record information in the form of text to extract one or more keywords which include at least one of a keyword relating to an experimental material, a keyword relating to a research and experiment process, and a keyword relating to a research result, and selecting experiment-related data corresponding to the one or more extracted keywords on the basis of the prestored experiment-related data and autocompleting research record information corresponding to the one or more extracted keywords using the selected experiment-related data.

The acquiring of the research record information may include acquiring equipment usage information from sensors each provided in a plurality of pieces of equipment used in research and experiments and acquiring material usage information from sensors each provided in a plurality of material used in the research and experiments, and the processing of the acquired research record information may include generating processed research record information using the acquired equipment usage information and the acquired material usage information.

The acquired research record information may include a keyword relating to an experimental material, a keyword relating to a research and experiment process, and a keyword relating to a research result, and the processing of the acquired research record information may include autocompleting the keyword relating to the experimental material using data included in the prestored experiment-related data to generate experimental material information and synchronizing the generated experimental material information with data included in the prestored experiment-related data and related to experimental materials, autocompleting the keyword relating to the research and experiment process using data included in the prestored experiment-related data and related to the experimental materials to generate research and experiment process information and synchronizing the generated research and experiment process information with the data included in the prestored experiment-related data and related to experimental materials, and visualizing the keyword relating to the research result on the basis of a preset result data format.

The method may further include generating research record information in the form of prose including one or more text sentences using a research record graph corresponding to the standardized research record data as input data for a pretrained second model. The pretrained second model may include a graph data learning model employing a graph attention network and may be a natural language processing model based on a transformer structure including an encoder and a decoder.

The generating of the research record information in the form of prose including the one or more text sentences may include, when a first user requests text conversion of first standardized research record data, generating a first research record graph from the first standardized research record data, generating research record information in a first prose form using the generated first research record graph and providing the generated research record information in the first prose form to the first user, and when at least a part of the provided research record information in the first prose form is modified by the first user, retraining the pretrained second model using the research record information in the first prose form at least the part of which is modified and the first research record graph as training data.

The generating of the standardized research record data may include generating the first research record graph using the first standardized research record data and simulating an experiment according to an experimental material, experimental equipment, and an experimental process included in the first standardized research record data using the generated first research record graph and matching and storing results of simulating the experiment and the first standardized research record data.

Another aspect of the present invention provides a device for automatically generating standardized research record data for training an artificial intelligence model, the device including a processor, a network interface, a memory, and a computer program loaded into the memory and executed by the processor. The computer program may include an instruction to acquire research record information of an experiment, an instruction to process the acquired research record information on the basis of prestored experiment-related data, and an instruction to generate standardized research record data using the processed research record information.

Another aspect of the present invention provides a computer program recorded on a computer-readable recording medium to perform a method of automatically generating standardized research record data for training an artificial intelligence model, the method including acquiring research record information of an experiment, processing the acquired research record information on the basis of pre-stored experiment-related data, and generating standardized research record data using the processed research record information Other details of the present invention are included in the detailed description and drawings.

Advantageous Effects

According to various embodiments of the present invention, it is possible to increase the convenience of recording, greatly improve the accuracy of records, and facilitate analysis, sharing, and management of research processes and results by processing non-standardized research record information and automatically generating standardized research record data and also assist in developing synthetic materials more conveniently and quickly by providing a synthetic material development process for drawing information on synthetic materials which satisfy specific conditions, and guide information for synthesizing the synthetic materials through an artificial intelligence model which is trained using research record data standardized according to the above method as training data.

Effects of the present invention are not limited to that described above, and other effects which have not been described will be clearly understood by those of ordinary skill in the art from the following description.

DESCRIPTION OF DRAWINGS

FIGS. 5 to 7 are diagrams illustrating a process of automatically generating standardized research record data using research record information in the form of prose according to various embodiments.

FIG. 9 is a diagram illustrating a process of automatically generating standardized research record data through a keyword input according to various embodiments.

FIG. 10 is a diagram illustrating a process of automatically generating standardized research record data using research record information in the form of voice according to various embodiments.

FIG. 11 is a flowchart illustrating a method of generating research record information in the form of prose using standardized research record data according to various embodiments.

FIGS. 12 to 14 are diagrams illustrating a process of generating research record information in the form of prose using standardized research record data according to various embodiments.

FIG. 19 is a diagram illustrating a process of recommending and providing non-standardized data on the basis of standardized research record data according to various embodiments.

MODES OF THE INVENTION

Figure 1:
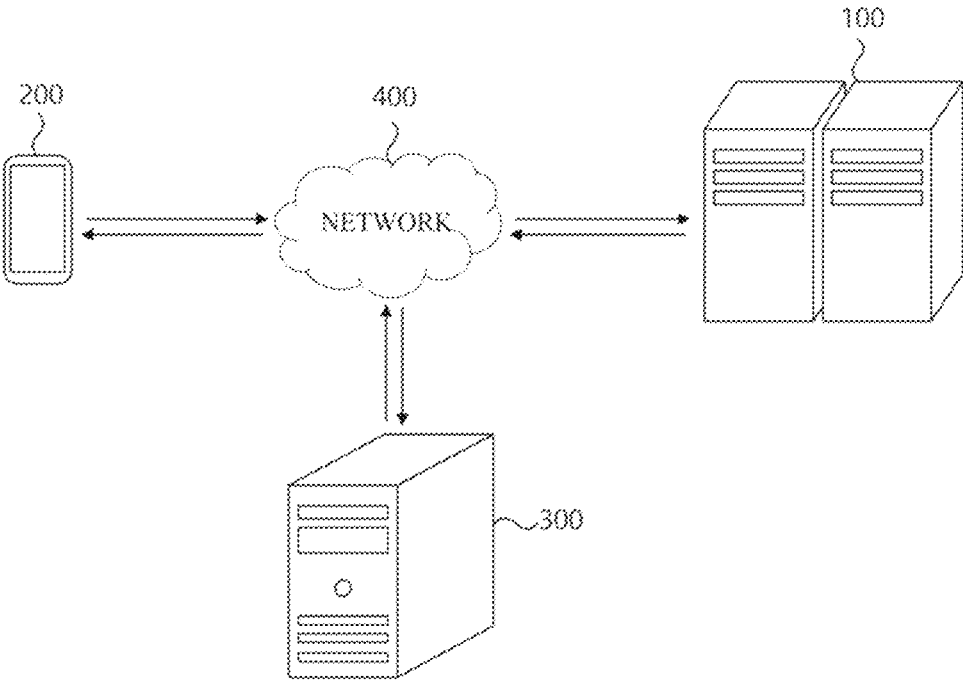
FIG. 1 is a diagram of a system for automatically generating standardized research record data for training an artificial intelligence model according to an embodiment of the present invention.

Advantages and features of the present invention and methods of achieving them will become apparent with reference to embodiments described in detail below with the accompanying drawings. However, the present invention is not limited to the embodiments disclosed below and can be implemented in various different forms. The embodiments are only provided to make the disclosure of the present invention complete and fully convey the scope of the present invention to those skilled in the technical field to which the present invention pertains. The present invention is only defined by the scope of the claims.

The terminology used herein is for the purpose of describing the embodiments and is not intended to limit the present invention. In this specification, a singular form also includes a plural form unless a phrase specifically states otherwise. As used in this specification, "comprises" and/or "comprising" do not exclude the presence or addition of one or more components other than stated components. Throughout the specification, the like reference numerals refer to like components, and "and/or" includes each and all combinations of one or more stated components. Although the terms "first," "second," etc. are used to describe various components, these components are not limited by these terms. These terms are only used to distinguish one component from others. Accordingly, a first component mentioned below may be a second component within the technical spirit of the present invention.

Unless otherwise defined, all terms (including technical and scientific terms) used herein may be used with the meaning commonly understood by those skilled in the technical field to which the present invention pertains. In addition, terms defined in a commonly used dictionary are not to be interpreted ideally or excessively unless specifically defined explicitly.

As used herein, the term "unit" or "module" refers to a software component or a hardware component such as a field programmable gate array (FPGA) or an application-specific integrated circuit (ASIC), and the "unit" or "module" performs certain roles. However, the "unit" or "module" is not limited to software or hardware. The "unit" or "module" may be configured to reside on an addressable storage medium or run on one or more processors. Accordingly, as an example, the "unit" or "module" includes components, such as software components, object-oriented software components, class components, and task components, processes, functions, attributes, procedures, subroutines, segments of program code, drivers, firmware, microcode, circuitry, data, databases (DBs), data structures, tables, arrays, and variables. Components and functions provided in "units" or "modules" may be combined into a smaller number of components and "units" or "modules" or may be subdivided into additional components and "units" or "modules."

Spatially relative terms "below," "beneath," "lower," "above," "upper," etc. can be used to easily describe the relationship between a certain component and other components shown in the drawings. Spatially relative terms are to be understood as terms that include different directions of components during use or operation in addition to the directions illustrated in the drawings. For example, when a component illustrated in the drawings is turned over, the component described as "below" or "beneath" another component may be placed "above" the other component. Accordingly, the exemplary term "below" may include both directions, below and above. Components may also be oriented in other directions, and thus, spatially relative terms may be interpreted according to orientation.

In this specification, a computer denotes all types of hardware device including at least one processor and may be understood as collectively including software configurations operating in a corresponding hardware device according to embodiments. For example, a computer may be understood as, but is not limited to, a meaning including all of a smartphone, a tablet personal computer (PC), a desktop computer, a laptop computer, and a user client and an application running on each device.

Hereinafter, exemplary embodiments of the present invention will be described in detail with reference to the accompanying drawings.

Each step described in this specification is described as being performed by a computer, but the subject of each step is not limited thereto. At least a part of each step may be performed in different devices according to embodiments.

FIG. 1 is a diagram of a system for automatically generating standardized research record data for training an artificial intelligence model according to an embodiment of the present invention.

Referring to FIG. 1, the system for automatically generating standardized research record data for training an artificial intelligence model according to an embodiment of the present invention may include a device 100 for automatically generating standardized research record data, a user terminal 200, an external server 300, and a network 400.

The system for automatically generating standardized research record data for training an artificial intelligence model shown in FIG. 1 is according to an exemplary embodiment. Components of the system are not limited to the embodiment shown in FIG. 1 and may be added, changed, or removed as necessary. For example, the system for automatically generating standardized research record data for training an artificial intelligence model may not include the external server 300 for storing and managing various information and data and may store and manage various information and data using a storage space provided in the device 100 for automatically generating standardized research record data.

According to an exemplary embodiment, the device 100 for automatically generating standardized research record data may receive research record information of an experiment from a user and generate standardized research record data for training an artificial intelligence model by automatically processing and recording the received research record information according to a preset format.

Also, the device 100 for automatically generating standardized research record data may record and store the standardized research record data and generate coded research record data by coding the standardized research record data to compute various information included in the stored standardized research record data and virtually simulate a specific experiment. Here, the standardized research record data and the coded research record data may be stored in connection with each other.

According to various embodiments, the device 100 for automatically generating standardized research record data may provide a method of automatically generating standardized research record data for training an artificial intelligence model which predicts a synthetic material satisfying a specific condition through an artificial intelligence model pretrained using research record data standardized according to the above method as training data and extracts and provides guide information for synthesizing the predicted synthetic material.

According to various embodiments, the device 100 for automatically generating standardized research record data may be connected to the user terminal 200 through the network 400 and provide a user interface (UI) (e.g., a graphic user interface (GUI) 10 in FIGS. 20 to 24) for providing a method of automatically generating standardized research record data for training an artificial intelligence model and a method of providing a synthetic material development process using an artificial intelligence model to the user terminal 200.

Here, the network 400 may be a connective structure in which a plurality of nodes, such as terminals and servers, can exchange information. For example, the network 400 may be a local area network (LAN), a wide area network (WAN), the Internet (World Wide Web (WWW)), a wired or wireless data communication network, a telephone network, a wired or wireless television communication network, etc.

Also, the wireless data communication network may be a $3^{rd}$ Generation (3G) network, a $4^{th}$ Generation (4G) network, a $5^{th}$ Generation (5G) network, a $3^{rd}$ Generation Partnership Project (3GPP) network, a $5^{th}$ Generation Partnership Project (5GPP) network, a Long Term Evolution (LTE) network, a World Interoperability for Microwave Access (WiMAX) network, a Wi-Fi, network, the Internet, a LAN, a wireless LAN, a WAN, a personal area network (PAN), a radio frequency (RF) network, a Bluetooth network, a Near-Field Communication (NFC) network, a satellite broadcasting network, an analog broadcasting network, a digital multimedia broadcasting (DMB) network, etc. However, the wireless data communication network is not limited thereto and may be one of other common-use networks which are applicable to the same or similar technical field.

According to various embodiments, the device 100 for automatically generating standardized research record data may generate standardized research record data on the basis of research record information input by a specific user and provide a standardized research record data sharing service of sharing the standardized research record data to other users.

For example, the device 100 for automatically generating standardized research record data may store and manage a plurality of pieces of standardized research record data which are generated on the basis of research record information input by a plurality of users and provide a search and presentation service of prestored standardized search record data to each of the plurality of users so that the users can search for and check their desired standardized research record data (e.g., check and simulate information recorded in the data) through the search and presentation service.

Also, the device 100 for automatically generating standardized research record data may provide an import function of externally obtaining and storing standardized research record data and an export function of sending prestored standardized research record data to each of the plurality of users so that the users can download a plurality of pieces of prestored research record data or upload externally generated standardized research record data.

Here, the device 100 for automatically generating standardized research record data supports various extensions to have wide compatibility such as converting standardized research record data to be externally sent according to a user's request, externally receiving uploads of standardized research record data having various extensions, etc.

According to various embodiments, the device 100 for automatically generating standardized research record data may provide a method of automatically generating standardized research record data for training an artificial intelligence model and a method of providing a synthetic material development process using an artificial intelligence model on the basis of a web or application according to a user's request, but a method provided by the device 100 for automatically generating standardized research record data is not limited thereto.

According to an exemplary embodiment, the user terminal 200 may be connected to the device 100 for automatically generating standardized research record data through the network 400, may input research record information through the UI provided by the device 100 for automatically generating standardized research record data, and may receive standardized research record data which is generated according to the research record information, in response to the input of the research record information.

Also, the user terminal 200 may input a specific condition through the UI provided by the device 100 for automatically generating standardized research record data and receive information on a synthetic material having a structure and properties satisfying the specific condition and guide information for synthesizing the synthetic material, in response to the input of the specific condition.

According to various embodiments, when an application provided by the device 100 for automatically generating standardized research record data is downloaded, installed, and executed, the user terminal 200 may receive the method of automatically generating standardized research record data for training an artificial intelligence model and the method of providing a synthetic material development process using an artificial intelligence model from the device 100 for automatically generating standardized research record data.

To this end, the user terminal 200 may be a smartphone that includes an operating system (OS) capable of running the application and includes a display for outputting the UI in at least a part thereof. However, the user terminal 200 is not limited thereto and may be, as a wireless communication device ensuring portability and mobility, any type of handheld wireless communication device such as a navigation device, a Personal Communication System (PCS) device, a Global System for Mobile communication (GSM) device, a Personal Digital Cellular (PDC) device, a Personal Handyphone System (PHS) device, a Personal Digital Assistant (PDA) device, an International Mobile Telecommunication (IMT)-2000 device, a Code Division Multiple Access (CDMA)-2000 device, a Wideband CDMA (WCDMA) device, a Wireless Broadband Internet (WiBro) terminal, a smartpad, a tablet PC, etc.

According to an exemplary embodiment, the external server 300 may be connected to the device 100 for automatically generating standardized research record data through the network 400 and may store and manage various information/data (e.g., data related to an experimental material, data related to a research and experiment process, a format of result data, etc.) required for the device 100 for automatically generating standardized research record data to perform the method of automatically generating standardized research record data for training an artificial intelligence model and the method of providing a synthetic material development process using an artificial intelligence model or store and manage various information/data (e.g., standardized (or coded) research record data) generated by performing the method of automatically generating standardized research record data for training an artificial intelligence model and the method of providing a synthetic material development process using an artificial intelligence model.

Here, the external server 300 may be, but is not limited to, a storage server separately provided outside the device 100 for automatically generating standardized research record data. A hardware configuration of the device 100 for automatically generating standardized research record data will be described below with reference to FIG. 2.

Figure 2:
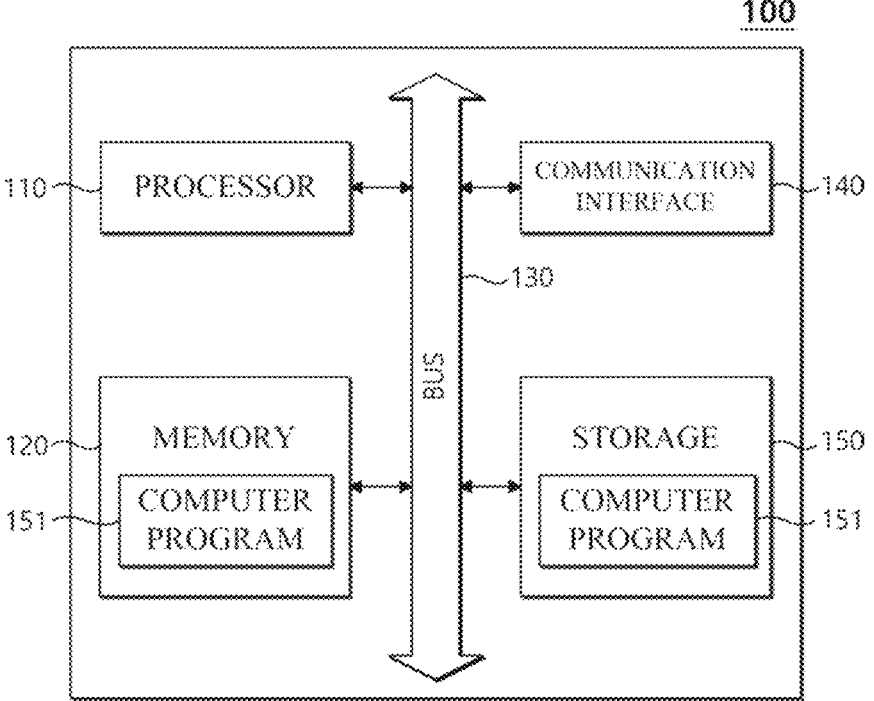
FIG. 2 is a hardware block diagram of a device for automatically generating standardized research record data for training an artificial intelligence model according to another embodiment of the present invention.

FIG. 2 is a hardware block diagram of a device for automatically generating standardized research record data for training an artificial intelligence model according to another embodiment of the present invention.

Referring to FIG. 2, the device 100 for automatically generating standardized research record data (hereinafter, the "computing device 100") may include at least one processor 110, a memory 120 into which a computer program 151 executed by the processor 110 is loaded, a bus 130, a communication interface 140, and a storage 150 which stores the computer program 151. Here, only components related to embodiments of the present invention are shown in FIG. 2. Accordingly, those skilled in the technical field to which the present invention pertains should appreciate that general-use components other than the components shown in FIG. 2 may be additionally included.

The processor 110 controls overall operations of each component of the computing device 100. The processor 110 may include a central processing unit (CPU), a microprocessor unit (MPC), a micro-controller unit (MCU), a graphic processing unit (GPU) or any form of processor well known in the technical field of the present invention.

Also, the processor 110 may perform calculation for at least one application or program for executing methods according to exemplary embodiments of the present invention, and the computing device 100 may include at least one processor.

According to various embodiments, the processor 110 may further include a random access memory (RAM; not shown) and a read-only memory (ROM) which temporarily and/or permanently store a signal (or data) processed in the processor 110. Also, the processor 110 may be implemented in the form of a system on chip (SoC) including at least one of a GPU, a RAM, and a ROM.

The memory 120 stores various data, instructions, and/or information. The computer program 151 may be loaded into the memory 120 from the storage 150 to perform methods or operations according to various embodiments of the present invention. When the computer program 151 is loaded into the memory 120, the processor 110 may perform the methods or operations by executing one or more instructions constituting the computer program 151. The memory 120 may be implemented as a volatile memory, such as a RAM, but the technical scope of the present disclosure is not limited thereto.

The bus 130 provides a communication function between the components of the computing device 100. The bus 130 may be implemented in one of various forms of buses such as an address bus, a data bus, a control bus, etc.

The communication interface 140 supports wired or wireless Internet communication of the computing device 100. Also, the communication interface 140 may support various communication methods other than Internet communication. To this end, the communication interface 140 may include a communication module well known in the technical field of the present invention. According to some embodiments, the communication interface 140 may be omitted.

The storage 150 may non-temporarily store the computer program 151. When the computing device 100 performs the method of automatically generating standardized research record data for training an artificial intelligence model and the method of providing a synthetic material development process using an artificial intelligence model, the storage 150 may store various information required for providing the method of automatically generating standardized research record data for training an artificial intelligence model and the method of providing a synthetic material development process using an artificial intelligence model.

The storage 150 may include a non-volatile memory, such as a ROM, an erasable programmable ROM (EPROM), an electrically erasable PROM (EEPROM), flash memory, etc., a hard disk, a removable disk, or any form of computer-readable recording medium well known in the technical field to which the present invention pertains.

The computer program 151 may include one or more instructions which cause the processor 110 to perform methods or operations according to various embodiments of the present invention when loaded into the memory 120. In other words, the processor 110 may perform the methods/operations according to various embodiments of the present invention by executing the one or more instructions.

According to an exemplary embodiment, the computer program 151 may include one or more instructions for performing the method of automatically generating standardized research record data for training an artificial intelligence model which includes a step of acquiring research record information of an experiment, a step of processing the acquired research record information on the basis of prestored experiment-related data, and a step of generating standardized research record data using the processed research record information.

Also, the computer program 151 may include one or more instructions for performing the method of providing a synthetic material development process using an artificial intelligence model which includes a step of acquiring at least one condition and a step of extracting information on a synthetic material satisfying the acquired at least one condition and extracting guide information for synthesizing the synthetic material on the basis of the extracted information on the synthetic material.

Steps of the methods or algorithms described in connection with exemplary embodiments of the present invention may be directly implemented as hardware, software modules executed by hardware, or a combination thereof. The software modules may reside in a RAM, a ROM, an EPROM, an EEPROM, a flash memory, a hard disk, a removable disk, a compact disc (CD)-ROM, or any form of computer-readable recording medium well known in the technical field to which the present invention pertains.

Components of the present invention may be implemented as a program (or application) and stored in a medium so as to be executed in combination with a computer which is hardware. Components of the present invention may be executed by software programming or software elements. Similarly, embodiments may be implemented in a programming or scripting language, such as C, C++, Java, assembler, etc., to include various algorithms which are embodied as combinations of data structures, processes, routines, or other programming elements. Functional aspects may be implemented as an algorithm executed by one or more processors. The method of automatically generating standardized research record data for training an artificial intelligence model which is performed by the computing device 100 will be described below with reference to FIGS. 3 to 15.

Figure 3:
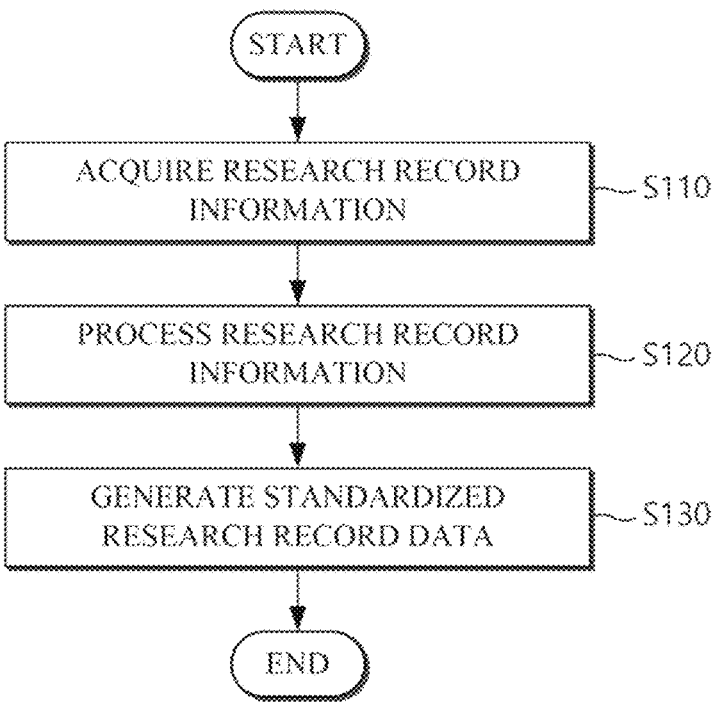
FIG. 3 is a flowchart illustrating a method of automatically generating standardized research record data for training an artificial intelligence model according to various embodiments.

FIG. 3 is a flowchart illustrating a method of automatically generating standardized research record data for training an artificial intelligence model according to various embodiments.

Referring to FIG. 3, in step S110, the computing device 100 may acquire research record information of an experiment.

Here, the research record information may be information generated when a user conducts the experiment or research.

For example, the research record information may include, but is not limited to, information on an experimental material, information on experimental equipment, information on a research and experiment process, and information on experiment and research results.

According to various embodiments, the computing device 100 may receive the research record information of the experiment (e.g., the information on the experimental material, the information on the experimental equipment, the information on the research and experiment process, and the information on the experiment and research results) which is generated when the user conducts the experiment or research, directly from the user.

According to various embodiments, the computing device 100 may collect research information (e.g., materials, equipment, attributes, research processes, experimental methods, etc.) of experiments conducted by major domestic and foreign bio-nano manufacturers by web crawling. However, a method of acquiring research record information is not limited thereto, and any method of acquiring research record information is applicable.

In step S120, the computing device 100 may process the research record information acquired through step S110. For example, the computing device 100 may process a plurality of pieces of information included in the research record information into a form for generating standardized research record data such as extracting only main keywords (e.g., keywords indicating a material, a synthesis method, etc.) from the research record information acquired through step S110 on the basis of prestored experiment-related data.

According to various embodiments, the computing device 100 may store the processed research record information in connection with the prestored experiment-related data. For example, the computing device 100 may store experimental material information generated by processing a keyword relating to the experimental material included in the research record information in connection with data related to experimental materials included in the prestored experiment-related data and store research and experiment process information generated by processing a keyword relating to the research and experiment process included in the research record information in connection with the data relating to the research and experiment process included in the prestored experiment-related data. In this way, check of accurate sample information is made possible.

Also, the computing device 100 may visualize keywords relating to the research results input by the user (e.g., into images or a graph) on the basis of a preset result data format.

Figure 23:
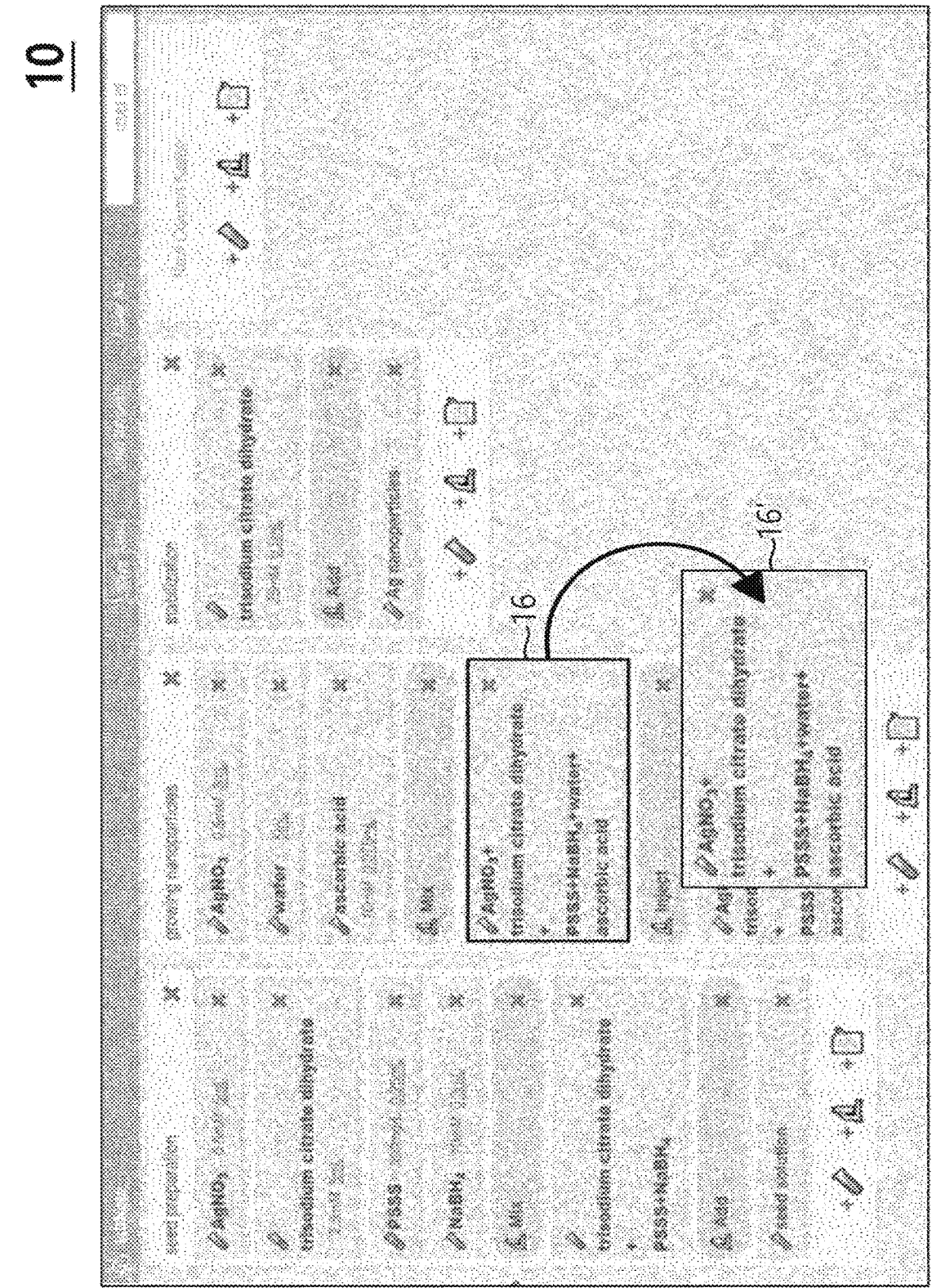
Figure 24:
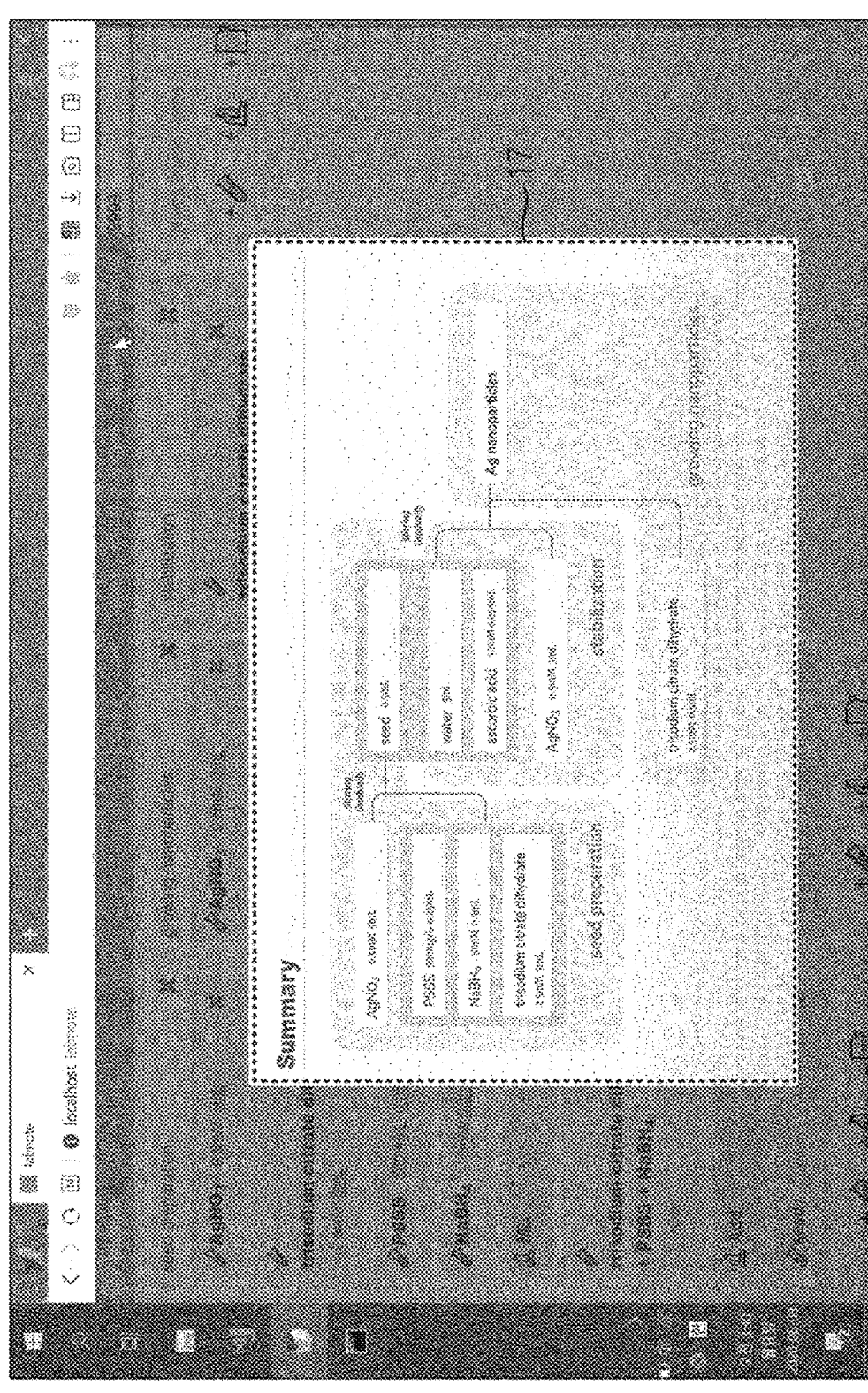

In step S130, the computing device 100 may generate standardized research record data LabNote using the research record information processed through step S120. For example, as shown in FIG. 23, the computing device 100 may generate standardized research record data by templating the processed research record information (e.g., the experimental material information, the research and experiment process information, and the visualized research results). A method of processing research record information according to a form of research record information will be described below with reference to FIGS. 4 to 12.

Figure 4:
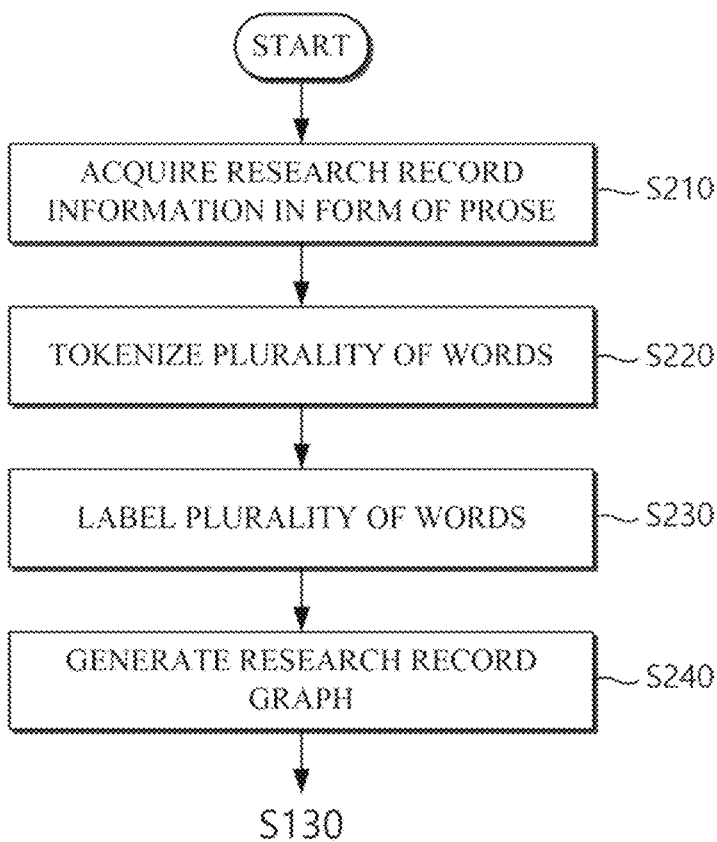
FIG. 4 is a flowchart illustrating a method of automatically generating standardized research record data using research record information in the form of prose according to various embodiments.
Figure 5:
Figure 6:
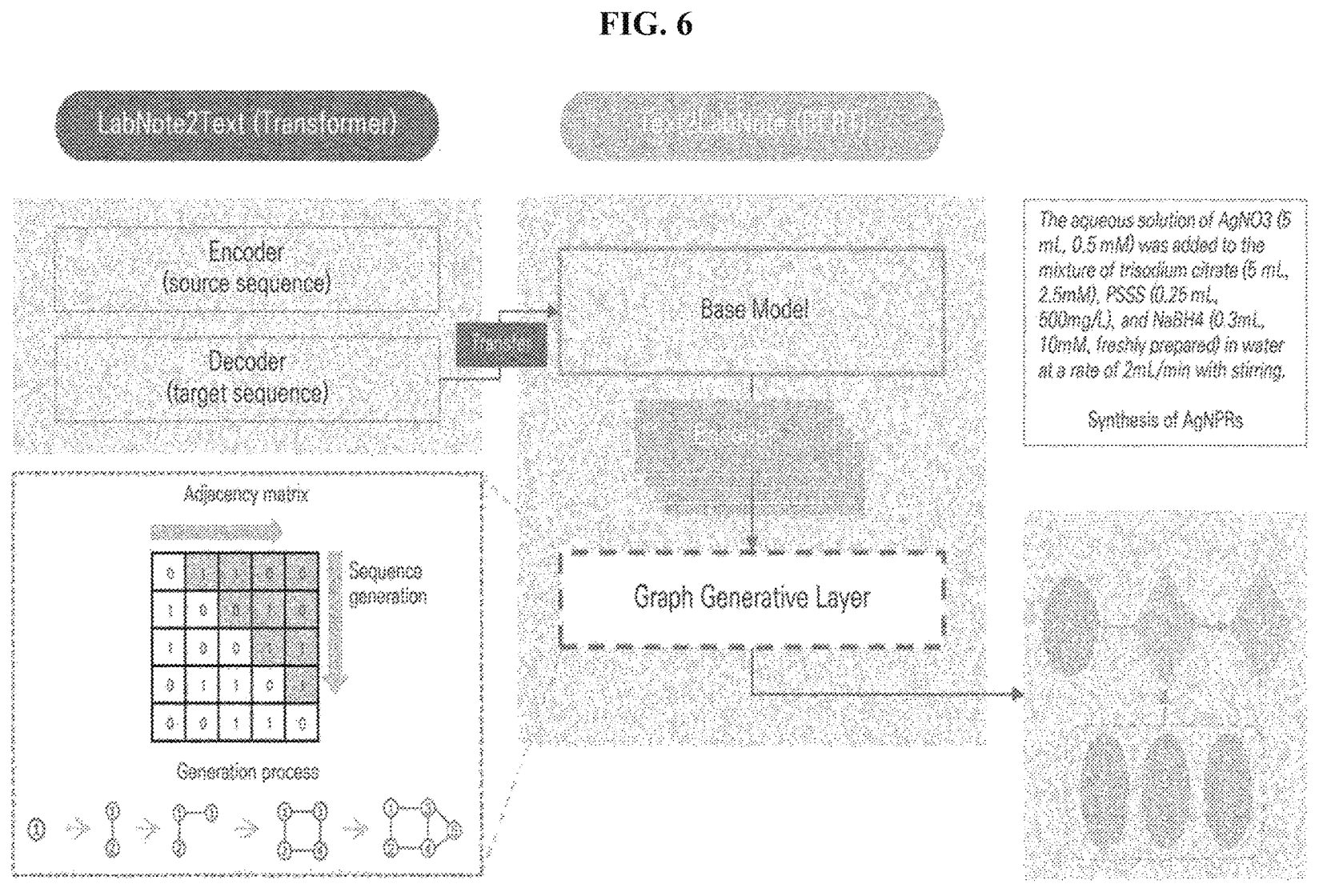
Figure 7:
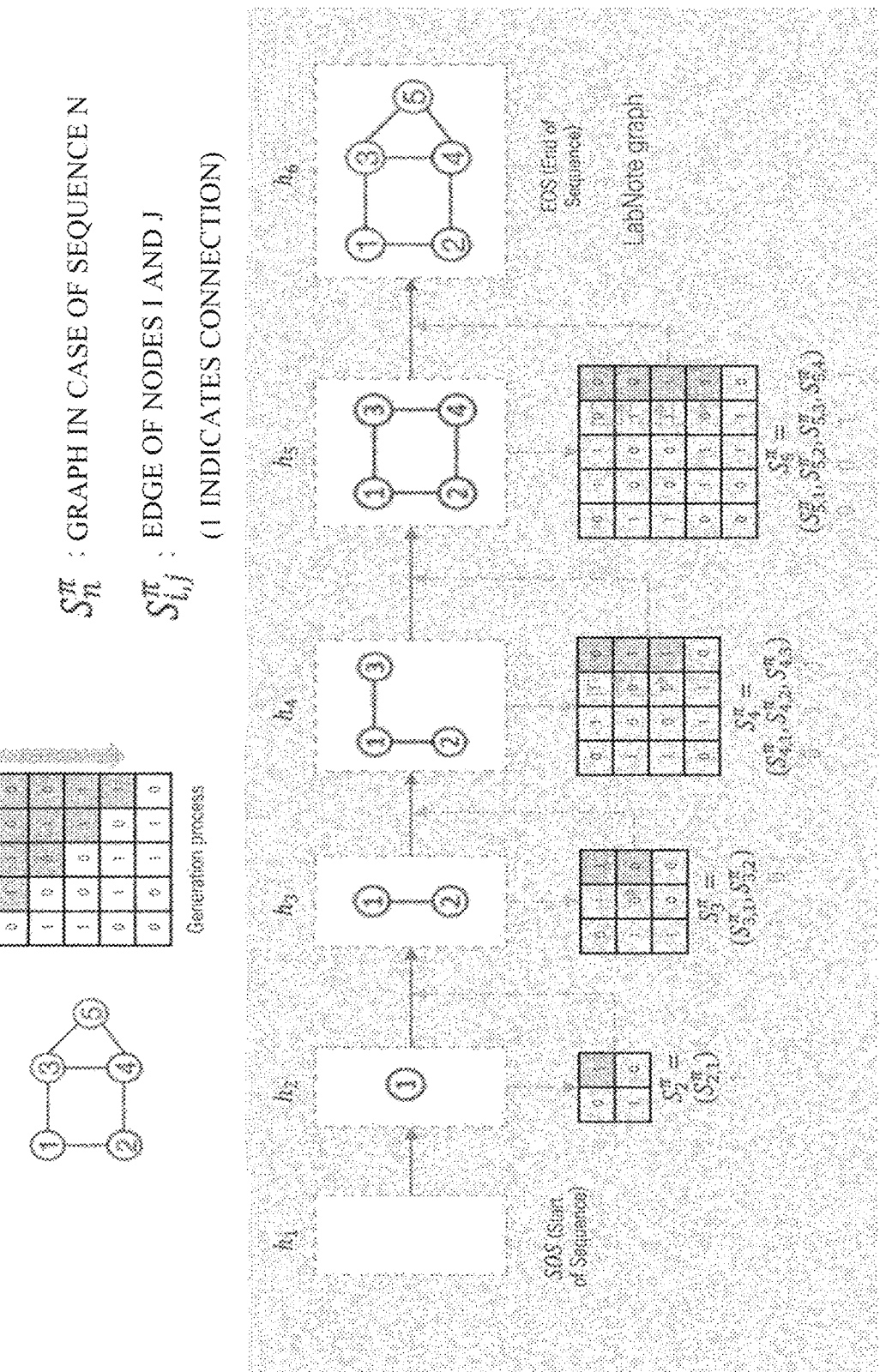

FIG. 4 is a flowchart illustrating a method of automatically generating standardized research record data using research record information in the form of prose according to various embodiments, and FIGS. 5 to 7 are diagrams illustrating a process of automatically generating standardized research record data using research record information in the form of prose according to various embodiments.

Referring to FIGS. 4 to 7, in step S210, the computing device 100 may acquire research record information in the form of prose including one or more text sentences (e.g., 21 in FIG. 5).

According to various embodiments, the computing device 100 may receive research record information which is recorded in the form of prose or handwriting including one or more sentences directly from the user.

According to various embodiments, the computing device 100 may externally acquire research record information in the form of prose including one or more sentences through web crawling or the like. However, a method of collecting research record information is not limited thereto.

In step S220, the computing device 100 may tokenize (e.g., 22 in FIG. 5) each of a plurality of words included in the research record information in the form of prose on the basis of prestored experiment-related data (e.g., a DB of experiment and research-related words selected from research papers and patents). For example, the computing device 100 may tokenize each of the plurality of words in a way of maximizing the likelihood of a corpus with a modified algorithm of byte pair encoding (BPE) (an information compression algorithm widely used in natural language processing models) through a WordPiece Model (WPM).

Here, the meaning of a tokenized word may be one word but is not limited thereto. In some cases, the meaning of a tokenized word may be a phrase, a clause, or a sentence including two or more words. For example, "aqueous solution" includes two words "aqueous" and "solution," but the two words represent one meaning in combination. Accordingly, a plurality of words may be classified/grouped in units of meanings and separately tokenized.

According to various embodiments, the computing device 100 may analyze the research record information in the form of prose to extract a keyword relating to an experimental material, a keyword relating to a research and experiment process, and a keyword relating to research results and may selectively tokenize only words corresponding to the extracted keywords.

According to various embodiments, the computing device 100 may analyze (e.g., optical character recognition (OCR) analysis or the like) research record information in the form of prose to extract a plurality of keywords from the research record information in the form of prose and may classify the plurality of extracted keywords as keywords relating to experimental materials, keywords relating to research and experiment processes, and keywords relating to research results by matching the plurality of extracted keywords with data (e.g., keyword data for each experimental material, keyword data for each research and experiment process, and keyword data for each research result) prestored in the DB.

In other words, the computing device 100 may determine which one of an experimental material, a research and experiment process, and a research result each of the plurality of keywords extracted from the research record information in the form of prose indicates on the basis of the prestored keyword data for each experimental material, keyword data for each research and experiment process, and keyword data for each research result and classify the keywords into categories according to determination results.

The computing device 100 may perform a string analysis and keyword extraction operation using an artificial intelligence model which is pretrained using the prestored keyword data for each experimental material, keyword data for each research and experiment process, and keyword data for each research result as training data, but a method of performing the string analysis and keyword extraction operation is not limited thereto.

According to various embodiments, the computing device 100 may analyze the research record information in the form of prose to extract a keyword relating to an experimental material, a keyword relating to a research and experiment process, and a keyword relating to research results. However, when none of the extracted keywords corresponds to information required for generating standardized research record data, the computing device 100 may repeatedly reanalyze the research record information in the form of prose until a corresponding keyword is extracted.

When any relevant keyword is not extracted regardless of a preset number (N times) of analyses on the research record information in the form of prose, the computing device 100 may provide guide information for requesting that information corresponding to a relevant keyword be input. In this way, in the case of generating standardized research record data, it is possible to make the user input important conditions and information which should be essentially input without omission.

In step S230, the computing device 100 may generate research record information in which each of the plurality of words is labeled with attribute information, that is, processed research record information, by labeling each of the plurality of words tokenized through step S220 with attribute information (e.g., 23 in FIG. 5). For example, the computing device 100 may determine an attribute of each of the plurality of words on the basis of the prestored experiment-related data (e.g., the DB of experiment and research-related words selected from papers and patents) and label each of the plurality of words with attribute information according to the determined attribute.

According to various embodiments, the tokenized words may be labeled through named entity recognition.

In step S240, the computing device 100 may generate a research record graph using the processed research record information generated through step S230. Also, the computing device 100 may generate standardized research record data using the research record graph.

According to various embodiments, the computing device 100 may generate the research record graph using a pretrained first model (Text2Labnote model).

As shown in FIG. 6, the pretrained first model may be a domain language learning model (e.g., a bidirectional encoder representations from transformers (BERT) model) based on transformer structure including a plurality of encoders.

Also, the pretrained first model may be, but is not limited to, a model trained using, as training information, a plurality of pieces of research record information in the form of prose and a plurality of research record graphs each corresponding to the plurality of pieces of research record information in the form of prose.

First, the computing device 100 may generate an adjacency matrix using the processed research record information including the plurality of words labeled with attribute information as input data for the pretrained first model.

Subsequently, the computing device 100 may generate a research record graph using the adjacency matrix. Here, the research record graph may include, but is not limited to, nodes each corresponding to the plurality of words and edges connecting the plurality of words. For example, as shown in FIG. 7, the computing device 100 may determine the connection relationship between node i and node j using a cell value $S_{ij}^*$ of a cell of row i and column j in the adjacency matrix and generate a research record graph by not connecting or connecting the plurality of nodes according to the connection relationships between the plurality of nodes.

Subsequently, the computing device 100 may generate standardized research record data using the generated research record graph (e.g., step S130). For example, as shown in FIG. 23, the computing device 100 may arrange cards 16 each corresponding to the plurality of words on a UI 10 and determine an arrangement form and arrangement order of the cards 16 each corresponding to the plurality of words according to the research record graph. However, a method of determining the arrangement form and arrangement order of the cards 16 is not limited thereto.

According to various embodiments, the computing device 100 may convert not only research record information written in the form of text by an electronic device but also research record information manually written by the user into standardized research record data through the first model. To this end, the computing device 100 may separately build the first model which learns research record information written in the form of text by an electronic device and standardized data corresponding to the research record data, and a second model which learns research record data having a handwritten form and standardized research record data corresponding to the research record data.

Figure 8:
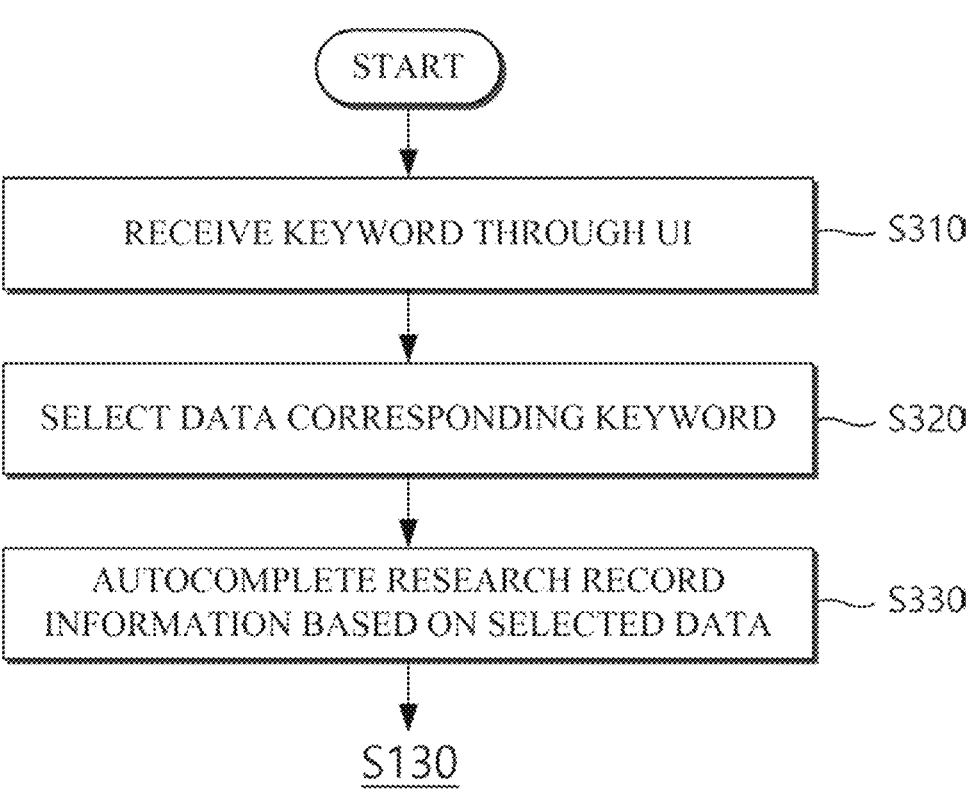
FIG. 8 is a flowchart illustrating a method of automatically generating standardized research record data through a keyword input according to various embodiments.

FIG. 8 is a flowchart illustrating a method of automatically generating standardized research record data through a keyword input according to various embodiments, and FIG. 9 is a diagram illustrating a process of automatically generating standardized research record data through a keyword input according to various embodiments.

Referring to FIGS. 8 and 9, in step S310, the computing device 100 may provide a UI (e.g., 10 in FIGS. 21 to 24) for inputting research record information and receive a keyword including at least one of a keyword relating to an experimental material, a keyword relating to a research and experiment process, and a keyword relating to a research result through the UI as a search word.

Since the research record information includes information on the experimental material, the information on the experimental equipment, and the information on the experiment are research process, the UI 10 may have a function of receiving information on an experimental material, information on experimental equipment, and information on an experiment and research process.

Figure 21:
FIGS. 21 to 24 are diagrams illustrating forms of user interfaces (UIs) applicable to various embodiments.
Figure 22:

More specifically, first the computing device 100 may provide a UI 14 for inputting information on an experimental material in response to the user's selecting a first button 11 as shown in FIGS. 21 and 22. When the user selects the first button 11, the computing device 100 may provide the UI 14 for inputting information on an experimental material as a popup window, but a method of providing the UI 14 is not limited thereto.

Subsequently, the computing device 100 may receive a keyword relating to an experimental material through the UI 14 for inputting information on an experimental material. For example, the computing device 100 may receive a keyword relating to a nickname, a keyword relating to the symbol of a chemical element, a keyword relating to a product number, a keyword relating to a state, a keyword relating to a solvent, a keyword relating to volume, and a keyword relating to concentration (additionally, a comment on the corresponding experimental material) through the UI 14 for inputting information on an experimental material.

Although not shown in the drawings, like what has been described above, the computing device 100 may provide a UI for inputting information on experimental equipment in response to the user's selecting a second button 12 and receive a keyword relating to experimental equipment through the UI for inputting information on experimental equipment and may provide a UI for inputting information on an experiment and research process in response to the user's selecting a third button 13 and receive a keyword relating to an experiment and research process.

In step S320, the computing device 100 may select experiment-related data corresponding to one or more keywords input by the user on the basis of the prestored experiment-related data. For example, as shown in FIG. 9, when "acetic ac" is input as a keyword by the user, the computing device 100 may select data including information on acetic acid from the prestored experiment-related data, but a method of selecting experiment-related data is not limited thereto.

According to various embodiments, when a plurality of pieces of experiment-related data correspond to the one or more keywords input by the user, the computing device 100 may select one or more from among the plurality of pieces of experiment-related data on the basis of the user's search history and provide the one or more pieces of selected experiment-related data to the user as recommendation data, and the user may select any one of the one or more pieces of experiment-related data provided as the recommendation data. For example, when a plurality of pieces of data include information on acetic acid, the computing device 100 may provide a piece of data which is the finally searched (or selected) data or the most frequently searched (or selected) data as recommendation data from among the plurality of pieces of data on the basis of the user's search history.

According to various embodiments, when a plurality of pieces of experiment-related data correspond to the one or more keywords input by the user, the computing device 100 may select one or more from among the plurality of pieces of experiment-related data on the basis of search histories of a plurality of users in the same research field as the user and provide the one or more pieces of selected experiment-related data to the user as recommendation data.

In step S330, the computing device 100 may autocomplete research record information corresponding to the one or more keywords input by the user using the experiment-related data selected through step S320. However, a method of autocompleting research record information is not limited thereto. For example, the computing device 100 may automatically arrange information included in the data (the experiment-related data corresponding to the keywords) selected by the user on a template for generating standardized research record data.

Subsequently, the computing device 100 may generate standardized research record data using the autocompleted research record information. Here, a method of generating standardized research record data may be implemented in the same way as in step S130 of FIG. 3 but is not limited thereto.

FIG. 10 is a diagram illustrating a process of automatically generating standardized research record data using research record information in the form of voice according to various embodiments.

Referring to FIG. 10, in step S410, research record information in the form of voice may be acquired from a user through a UI. For example, the computing device 100 may be connected to the user terminal 200 through the network 400 and collect research record information in the form of voice input through a microphone separately provided in the user terminal 200 (e.g., a smartphone or a laptop PC) or an external microphone connected to the user terminal 200. However, a method of collecting research record information in the form of voice is not limited thereto.

In step S420, the computing device 100 may convert research record information in the form of voice acquired through step S410 into research record information in the form of text by performing natural language processing (NLP) on the research record information in the form of voice.

Here, various technologies have been disclosed as a method of converting information in the form of voice into the form of text by performing NLP on the information in the form of voice, and such well-known technologies may be selectively applied. Accordingly, a detailed method will not be described.

Also, the computing device 100 may analyze research record information in the form of text and extract one or more keywords. For example, the computing device 100 may perform a string analysis and keyword extraction operation using an artificial intelligence model which is pretrained using, as training data, prestored keyword data for each experimental material, prestored keyword data for each research and experiment process, and prestored keyword data for each research result, but a method of extracting keywords is not limited thereto.

According to various embodiments, when the research record information in the form of voice input in step S410 is input in real time through a voice input device provided in the user terminal 200, the computing device 100 may extract one or more keywords by analyzing (e.g., performing NLP) the research record information in the form of voice input in real time from a point in time at which the voice input device is driven.

When the drive of the voice input device is terminated, the computing device 100 may reanalyze all the research record information in the form of voice input through the voice input device to verify the one or more extracted keywords in real time. For example, the computing device 100 may reanalyze all the research record information in the form of voice to determine the validity (e.g., whether the extracted keywords are accurate or inaccurate) of the extracted keywords in real time or whether there is any keyword that has not been extracted.

In step S430, the computing device 100 may select experiment-related data corresponding to the one or more keywords extracted through step S420 on the basis of the prestored experiment-related data. A process of selecting experiment-related data corresponding to keywords may be implemented in the same or a similar way to step S320 of FIG. 8 but is not limited thereto.

In step S440, the computing device 100 may autocomplete research record information corresponding to the one or more keywords input by the user using the experiment-related data selected through step S430. A process of autocompleting research record data may be implemented in the same or a similar way to step S330 of FIG. 8 but is not limited thereto.

In step S450, the computing device 100 may acquire equipment usage information from sensors each provided in a plurality of pieces of equipment used in research and experiments, acquire material usage information from sensors each provided in a plurality of materials used in research and experiments, and recognize usage of equipment and materials through the acquired equipment usage information and the acquired material usage information, thereby generating processed research record information.

For example, the computing device 100 may be connected to sensors (e.g., a position sensor, a motion sensor, etc.) each provided in equipment used in research and experiments and recognize (e.g., a case in which the position of specific equipment moves to a preset distance or more, a case in which movement of specific equipment is detected, etc.) equipment usage information (e.g., whether equipment is used, a type of used equipment, etc.) on the basis of sensor data collected from the sensors.

Also, the computing device 100 may recognize and track material usage information (e.g., whether a material is used, the types and amounts of materials used, etc.) using radio frequency identification (RFID) tags attached to test material containers, reagent bottles, etc. However, a method of recognizing and tracking material usage information is not limited thereto. A process of generating research record information in the form of prose using standardized research record data will be described below with reference to FIGS. 12 to 14.

Subsequently, the computing device 100 may generate standardized research record data using the autocompleted research record information. Here, a method of generating standardized research record data may be implemented in the same way as in step S130 of FIG. 3 but is not limited thereto. A process of generating research record information in the form of prose using standardized research record data will be described below with reference to FIGS. 12 to 14.

Figure 12:
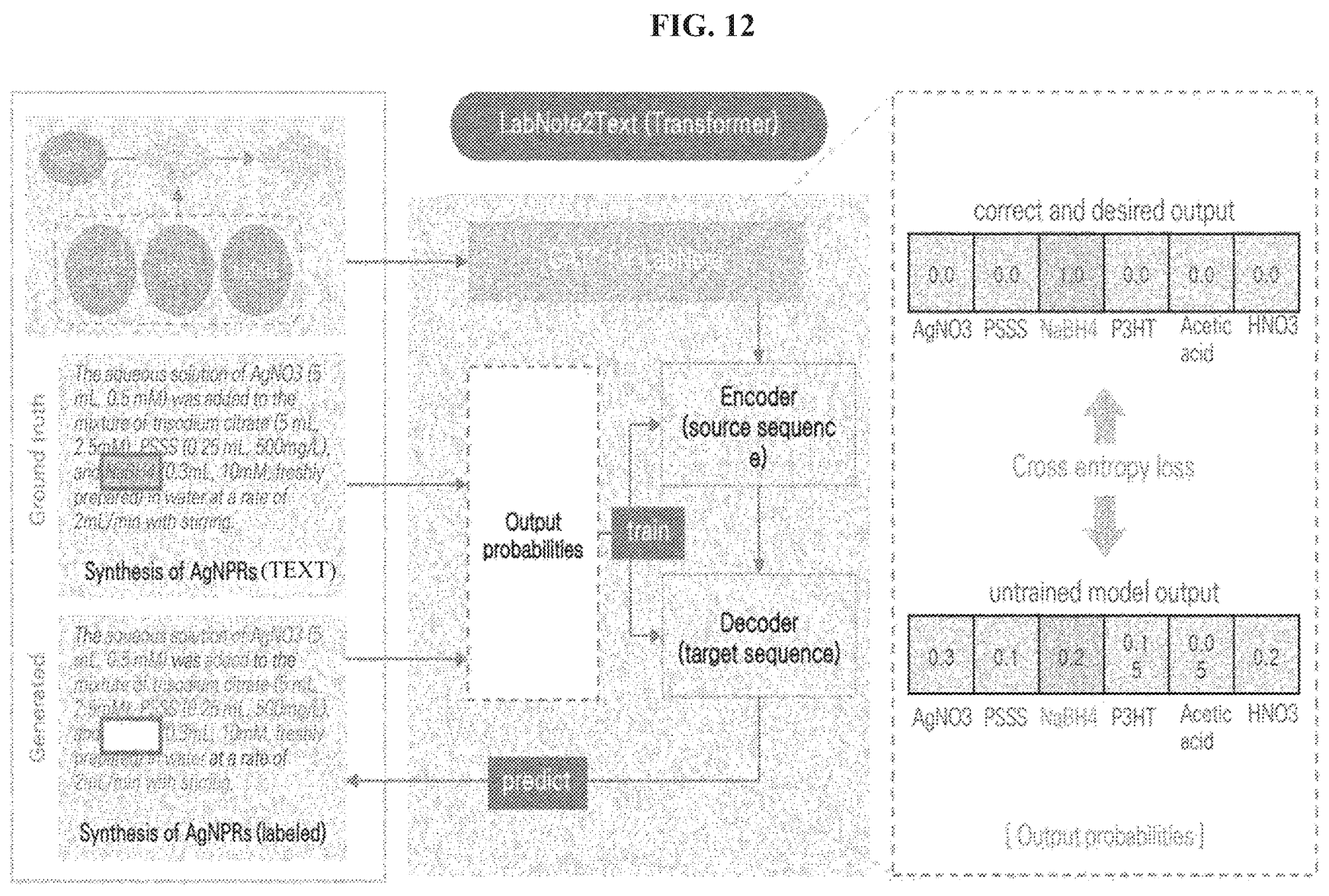
Figure 13:
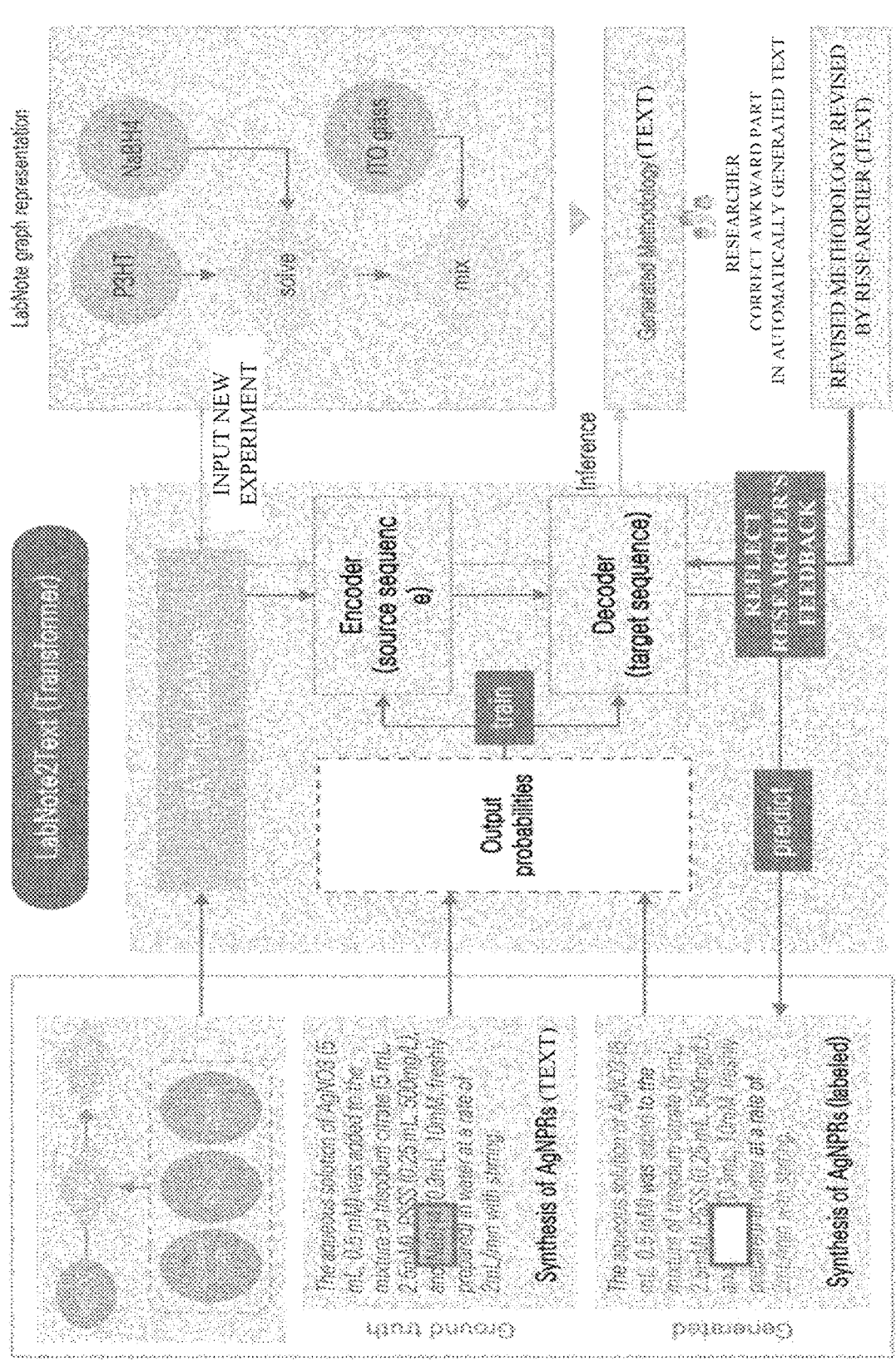
Figure 14:
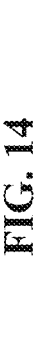

FIG. 11 is a flowchart illustrating a method of generating research record information in the form of prose using standardized research record data according to various embodiments, and FIGS. 12 to 14 are diagrams illustrating a process of generating research record information in the form of prose using standardized research record data according to various embodiments.

Referring to FIGS. 11 to 14, in step S510, the computing device 100 may acquire a request that research record information in the form of prose be generated which includes standardized research record data, from the user.

In step S520, the computing device 100 may generate a research record graph using the research record data included in the request that research record information in the form of prose be generated which is acquired through step S510. Here, the standardized research record data is generated on the basis of a research record graph, and thus the computing device 100 may generate the research record graph corresponding to the standardized research record data by inversely converting the standardized research record data. However, a method of generating a research record graph is not limited thereto.

In step S530, the computing device 100 may generate research record information in the form of prose including one or more text sentences using the research record graph generated through step S520.

According to various embodiments, the computing device 100 may generate research record information in the form of prose including one or more text sentences using the research record graph as input data for the pretrained second model (LabNote2Text model).

Here, the pretrained second model may be, but is not limited to, an NLP model (e.g., a sequence-to-sequence NLP model) based on a transformer structure including an encoder and a decoder as shown in FIGS. 12 and 13.

Also, the pretrained second model may be a graph data learning model employing an attention mechanism. A graph attention network (GAT) may be constructed or built to use standardized research record data converted into a research record graph as a base model of the second model as shown in FIG. 14, but the second model is not limited thereto.

Further, the pretrained second model may be, but is not limited to, a model trained using a plurality of pieces of research record information in the form of prose and a plurality of research record graphs each corresponding to the plurality of pieces of research record information in the form of prose as training data.

According to various embodiments, the computing device 100 may cause the first model and the second model to interoperate with each other and train the first model and the second model using input and output data. For example, the first model is a model that outputs a research record graph using research record information in the form of prose as an input, and the second model is a model that outputs research record information in the form of prose using a research record graph as an input. Accordingly, the first model and the second model may be trained using an output of the first model as an input for the second model and an output of the second model as an input for the first model, that is, using input and output data of each of the first model and the second model as training data.

Subsequently, the computing device 100 may provide the research record information in the form of prose generated according to the above method to the user.

In other words, when the user inputs research record information, standardized research record data is generated, and thus it is possible to easily manage and share research records. When the user tries to write a research record in the form of prose to write a paper, a patent specification, etc., it is possible to quickly and conveniently write the paper, the patent specification, etc. by converting the standardized research record data back into the research record information in the form of prose.

According to various embodiments, when a first user requests the computing device 100 to convert first standardized research record data into text, the computing device 100 may generate a first research record graph from the first standardized research record data, generate research record information in a first prose form using the generated first research record graph, and provide the generated research record information in the first prose form to the first user. When at least a part of the research record information in the first prose form is modified by the first user, the computing device 100 may retrain the pretrained second model using the research record information in the first prose form at least the part of which is modified and the first research record graph as training data. In this way, it is possible to improve the text conversion performance of standardized research record data.

According to various embodiments, the computing device 100 may simulate experiments and research using standardized research record data. This will be described below with reference to FIG. 15.

Figure 15:
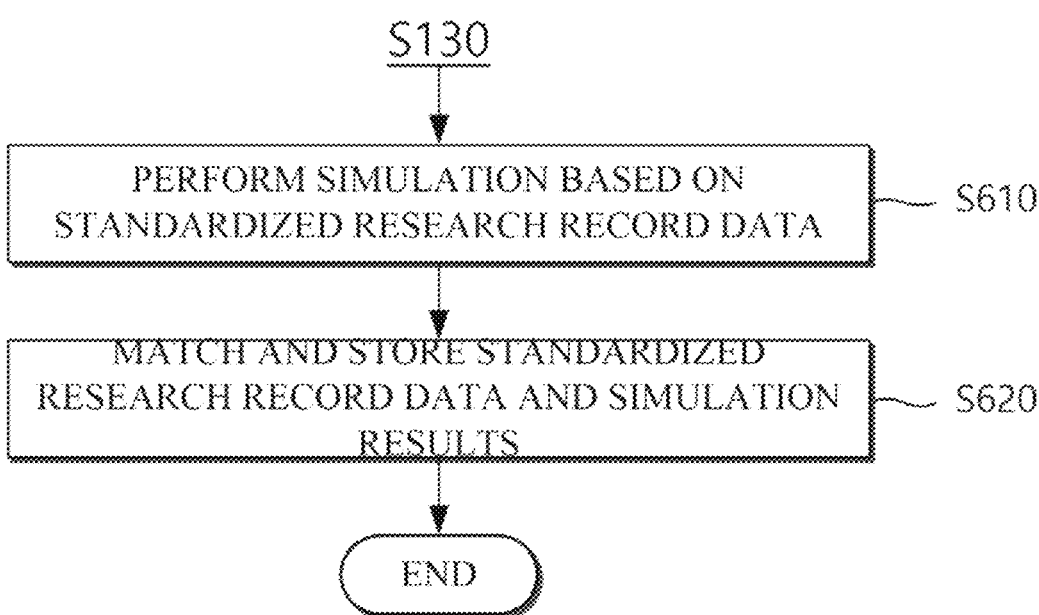
FIG. 15 is a flowchart illustrating a method of performing a simulation on the basis of standardized research record data according to various embodiments.

FIG. 15 is a flowchart illustrating a method of performing a simulation on the basis of standardized research record data according to various embodiments.

Referring to FIG. 15, in step S610, the computing device 100 may simulate an experiment according to an experiment material, experiment equipment, and an experiment process included in the first standardized research record data.

First, the computing device 100 may build a cloud lab (an unmanned autonomous laboratory or virtual lab) to perform an experimental simulation based on standardized research record data.

Here, the cloud lab is a platform-based research and experiment space employing a data sharing system, such as a cloud, and may be a space for virtually simulating specific research and experiments on the basis of externally obtained data (e.g., standardized research record data provided by the computing device 100) or sharing content and results of research and experiments with multiple users regardless of the time or location. Here, a method of building and using a cloud lab is a well-known technology. Accordingly, although a detailed method of building and using a cloud lab is not described herein, it will be easily appreciated by those of ordinary skill in the art.

Subsequently, the computing device 100 may generate coded research record data by converting standardized research record data into a form of computer-readable code to compute virtual research and experiments on the basis of standardized research record data, provide the generated coded researched record data to the cloud lab, and simulate an experiment based on the coded research record data by operating the cloud lab. For example, the computing device 100 may generate (code) a first research record graph using the first standardized research record data and simulate an experiment using the first research record graph according to the experiment material, the experiment equipment, and the experiment process included in the first standardized research record data. However, a method of simulating an experiment is not limited thereto.

Here, the experiment based on the coded research record data simulated through the cloud lab may be automatically simulated with all the standardized research record data every time standardized research record data is generated on the basis of research record information input by the user, or may be simulated with only specific standardized research record data when the user requests a simulation with the specific standardized research record data.

In step S620, the computing device 100 may match and store results (e.g., the structure and composition of a material, properties of the material, etc. drawn according to experimental materials and experimental processes included in the coded research record data) of simulating the experiment based on the coded research record through the cloud lab and the coded research record data used in the simulation.

Here, the cloud lab may additionally store the simulation results as research result information included in the coded research record data, and the computing device 100 may receive the coded research record data in which the simulation results are additionally stored from the cloud lab and store and manage the coded research record data. The method of providing a synthetic material development process using an artificial intelligence model which is performed by a computing device will be described below with reference to FIGS. 16 to 20.

Figure 16:
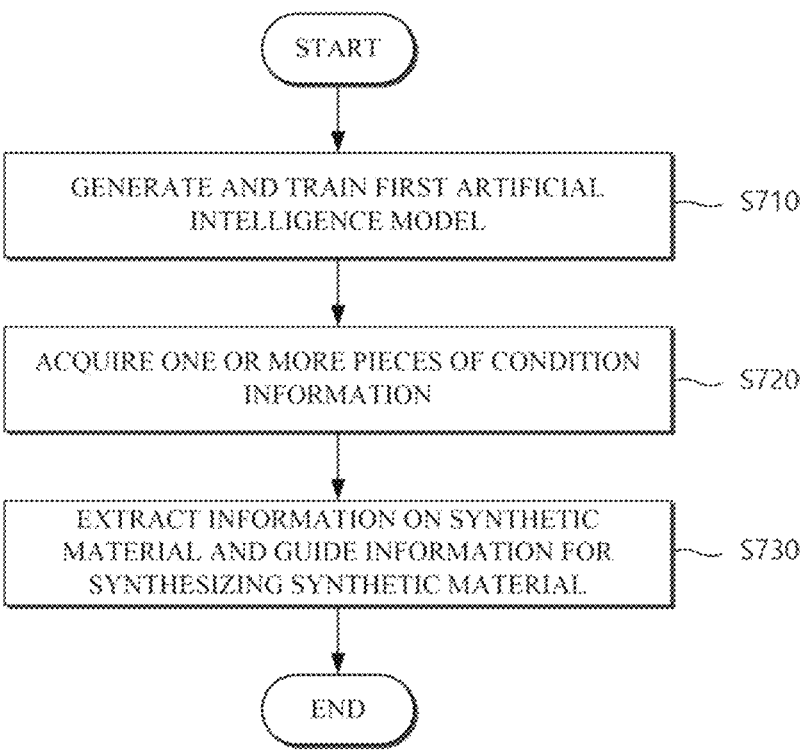
FIG. 16 is a flowchart illustrating a method of extracting information on a synthetic material and guide information for synthesizing the synthetic material through a first artificial intelligence model according to various embodiments.

FIG. 16 is a flowchart illustrating a method of extracting information on a synthetic material and guide information for synthesizing the synthetic material through a first artificial intelligence model according to various embodiments.

Figure 17:
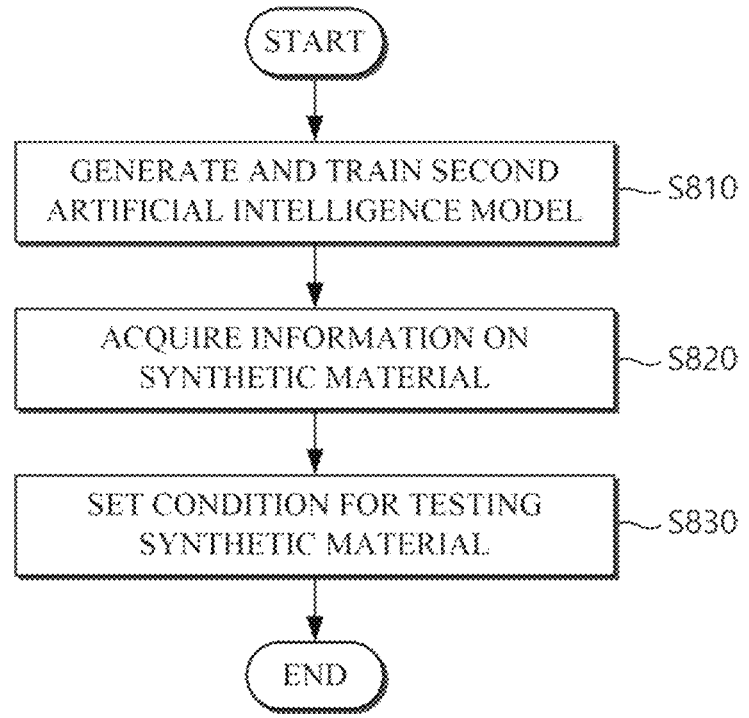
FIG. 17 is a flowchart illustrating a method of setting test conditions for a synthetic material through a second artificial intelligence model according to various embodiments.
Figure 18:
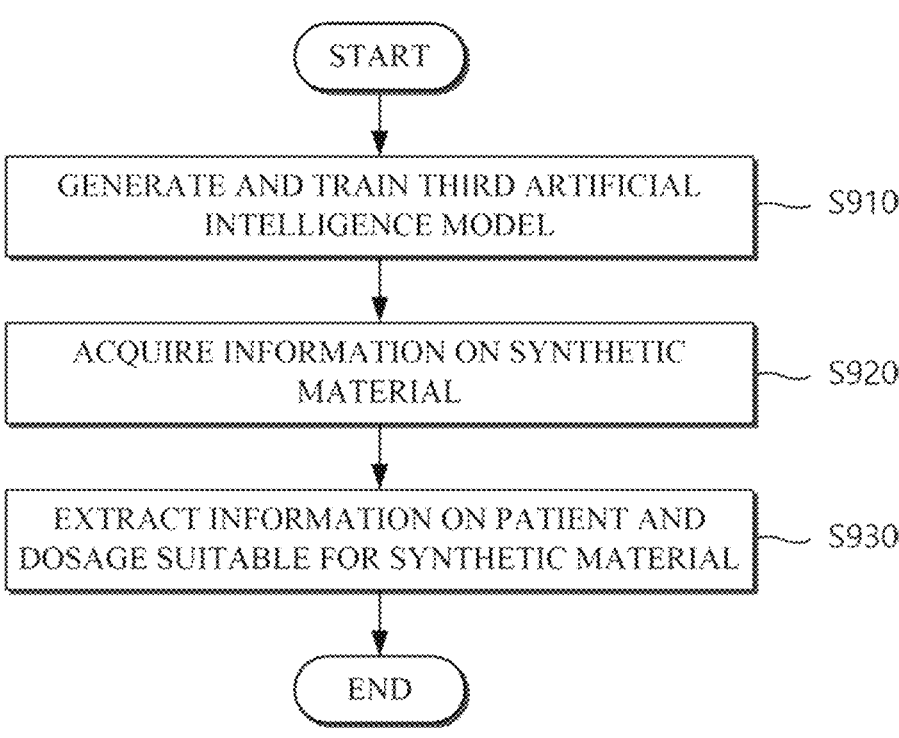
FIG. 18 is a diagram illustrating a method of drawing information on patients and dosages suitable for a new drug through a third artificial intelligence model in the case of developing the new drug according to various embodiments.

Referring to FIG. 16, the computing device 100 may extract and provide information on a synthetic material having a specific structure and specific properties and guide information for synthesizing the synthetic material. In FIGS. 16 to 18, a synthetic material is described as a candidate material for developing a new drug, but is not limited thereto.

New drug development is taken as an example below to describe a synthetic material development process according to a disclosed embodiment. However, the synthetic material development process according to the disclosed embodiment may be used for synthetic material development in various fields in addition to new drugs.

For example, the synthetic material development process according to the disclosed embodiment may be used for various purposes, such as synthetic material development for increasing heat resistance of semiconductor materials, synthetic material development for increasing electrical conductivity of battery materials, etc., and is not limited to a specific field.

In step S710, the computing device 100 may generate and train a first artificial intelligence model.

Here, the first artificial intelligence model (or a computation model, a neural network, or a network function) includes one or more network functions, and the one or more network functions may generally be sets of mutually connected calculation units which may be referred to as "nodes." The one or more network functions may include one or more nodes. The nodes (or neurons) constituting the one or more network functions may be connected to each other through one or more "links."

In the first artificial intelligence model, one or more nodes connected through a link may relatively have a relationship as an input node and an output node. The concepts of an input node and an output node are relative. Any node which is relatively an output node for one node may be an input node for another node, and vice versa. As described above, the relationship between an input node and an output node may be established on the basis of a link. One input node may be connected to one or more output nodes through links, and vice versa.

In the relationship between an input node and an output node connected through one link, a value of the output node may be determined on the basis of data input to the input node. Here, a node connecting the input node and the output node to each other may have a weight. The weight may be variable and varied by the user or an algorithm to perform a function required by the first artificial intelligence model. For example, when one or more input nodes and one output node are connected to each other through separate links, the output node may determine an output node value on the basis of values input to the input node connected to the output node and weights set for the links each corresponding to the input nodes.

As described above, in the first artificial intelligence model, one or more nodes are connected to each other through one or more links to have a relationship as an input node and an output node. Characteristics of the first artificial intelligence model may be determined according to the number of nodes, the number of links, connection relationships between nodes and links, and weight values each assigned to the links in the first artificial intelligence model. For example, when two first artificial intelligence models have the same number of nodes, the same number of links, and different weights for a link, the two first artificial intelligence models may be recognized to be different.

Some nodes constituting the first artificial intelligence model may constitute one layer on the basis of distances from an initial input node. For example, a set of nodes having a distance of n from the initial input node may constitute layer n. The distance from the initial input node may be defined according to the minimum number of links which should be passed through to reach a corresponding node from the initial input node. However, this definition of a layer is arbitrary description, and the order of a layer in the first artificial intelligence model may be defined according to a different method from that described above. For example, a layer of nodes may be defined according to the distance from a final output node.

The initial input node may be one or more of nodes to which data is directly input without passing through any link in the relationships with other nodes among nodes in the first artificial intelligence model. Alternatively, the initial input node may be nodes that do not have other input nodes connected through links in the link-based relationships between nodes within the first artificial intelligence model network. Similarly, the final output node may be one or more of nodes which have no output node in the relationships with other nodes among the nodes in the first artificial intelligence model. Also, hidden nodes may be nodes constituting the first artificial intelligence model other than the initial input node and the final output node. In the first artificial intelligence model according to an embodiment of the present disclosure, the number of nodes in the input layer may be larger than the number of nodes in a hidden layer close to the output layer, and the number of nodes may decrease from the input layer to the hidden layer.

The first artificial intelligence model may include one or more hidden layers. Hidden nodes of the hidden layers may use outputs of the previous layer and outputs of surrounding hidden nodes as inputs. The number of hidden nodes in each hidden layer may be the same as or different from the number of hidden nodes in other hidden layers. The number of nodes in the input layer may be determined on the basis of the number of data fields of input data and may be the same as or different from the number of hidden nodes. The input data input to the input layer may be calculated by the hidden nodes of the hidden layers, and a calculation result may be output by a fully connected layer (FCL) which is the output layer.

According to various embodiments, the computing device 100 may accumulate training data for training the first artificial intelligence model and train the first artificial intelligence model according to at least one method among supervised learning, unsupervised learning, and semi-supervised learning using the accumulated training data.

Training of the first artificial intelligence model is for the purpose of minimizing an error in outputs. Training of the first artificial intelligence model is a process of calculating an error between a target and an output of the first artificial intelligence model for training data by repeatedly inputting the training data to the first artificial intelligence model and updating the weight of each node of the first artificial intelligence model by backpropagating the error of the first artificial intelligence model from the output layer of the first artificial intelligence model toward the input layer of the first artificial intelligence model to reduce the error.

In the case of supervised learning, training data each labeled with correct answers (i.e., labeled training data) may be used, and in the case of non-supervised learning, each piece of training data may not be labeled with a correct answer. For example, in the case of supervised learning of data classification, training data may be data each labeled with categories. Labeled training data is input to the first artificial intelligence model, and an output (category) of the first artificial intelligence model is compared with a label of training data so that an error may be calculated.

As another example, in the case of non-supervised learning of data classification, training data which is an input is compared with an output of the first artificial intelligence model so that an error may be calculated. The calculated error may be backpropagated in the reverse direction (i.e., the direction from the output layer toward the input layer) in the first artificial intelligence model, and connection weights of nodes may be updated in each layer of the first artificial intelligence model due to the backpropagation. A variation of the connection weight of each node being updated may be determined according to a learning rate.

Calculation of the first artificial intelligence model for input data and backpropagation of an error may constitute a learning cycle (epoch). Different learning rates may be used according to the number of times the first artificial intelligence model repeats a learning cycle. For example, in the early learning stage of the first artificial intelligence model, a high learning rate may be used for the first artificial intelligence model to ensure a certain level of performance and improve efficiency, and in the late learning stage, a low learning rate may be used to increase accuracy.

In training of the first artificial intelligence model, training data may generally be a subset of actual data (i.e., data to be processed through a trained first artificial intelligence model). Accordingly, there may be a learning cycle in which an error for training data may be reduced, but an error for actual data may increase. Overfitting is such a phenomenon in which a model is excessively trained with training data and thus an error for actual data increases. For example, the first artificial intelligence model which learns cats from images of yellow cats may not recognize cats which are not yellow, and this may be overfitting.

Overfitting may result in an increase in the error of a machine learning algorithm. To prevent such overfitting, various optimization methods may be used. To prevent overfitting, the amount of training data may be increased, or a method, such as regularization, dropout of omitting some nodes of a network in a learning process, etc., may be used.

According to various embodiments, the computing device 100 may train the first artificial intelligence model using, as training data, attribute information (e.g., structure and property information) of each of a plurality of synthetic materials and information for synthesizing each of the plurality of synthetic materials (e.g., information on materials, equipment, synthesis methods, etc. for synthesizing each of the plurality of synthetic materials). However, training data for the first artificial intelligence model is not limited thereto, and the computing device 100 may train the first artificial intelligence model using yield information of each of a plurality of synthesis methods as training data.

In step S720, the computing device 100 may acquire one or more conditions from the user. Here, the one or more conditions may be properties of a synthetic material (e.g., being effective against a specific disease and the like) but is not limited thereto.

In step S730, the computing device 100 may predict a synthetic material having a structure and properties satisfying the one or more conditions using the one or more conditions acquired through step S720 as an input value and extract result values including materials, equipment, and synthesis methods for synthesizing the predicted synthetic material.

For example, when conditions input by the user are "to be effective against disease z and to have a yield of 90% or more," by inputting the conditions to the first artificial intelligence model, the computing device 100 may predict a synthetic material having a structure and properties optimized to be effective against disease z, determine materials for generating the predicted synthetic material according to the synthetic material, determine a synthesis method for synthesizing the synthetic material and also achieving a yield of 90% or more and equipment required for performing the synthesis method, and extract the synthesis method and the equipment as result values.

The first artificial intelligence model is a model trained using attribute information (e.g., structure and property information) of each of a plurality of synthetic materials and information for synthesizing each of the plurality of synthetic materials (e.g., materials, equipment, and synthesis methods for synthesizing each of the plurality of synthetic materials), and yield information of each of synthesis methods as training data in the form of "when synthesis is performed using a specific material, specific equipment, and a specific synthesis process, a specific synthetic material which is effective against a specific disease is generated at a yield of N %," that is, a model which learns correlation between attribute information of synthetic materials, information for synthesizing the synthetic materials, and yield information. Accordingly, with a simple operation of inputting a specific condition to the first artificial intelligence model, it is possible to extract a synthetic material satisfying the condition and guide information for generating the synthetic material.

In addition, since the first artificial intelligence model is a model which learns correlation between attribute information of synthetic materials, information for synthesizing the synthetic materials, and yield information, in reverse to the above operation, it is possible to extract information on a synthetic material predicted to be synthesized according to a specific material, equipment, and synthesis method as result values using the specific material, equipment, and synthesis method as input values for the first artificial intelligence model.

According to various embodiments, the computing device 100 may provide the result values to the user, receive feedback information (e.g., information on a synthetic material generated according to the material, equipment, and synthesis method for synthesizing the predicted synthetic material) from the user in response to the provided result values, and retrain the first artificial intelligence model using the received feedback information as training data.

Here, the computing device 100 can retrain the first artificial intelligence model using the feedback information as training data, only when the synthetic material predicted to be generated on the basis of the result values provided to the user differs from a synthetic material actually generated, on the basis of the feedback information input by the user.

According to various embodiments, in the case of scaling up the synthetic material predicted through the first artificial intelligence model, the computing device 100 may re-extract a synthesis method for synthesizing the synthetic material through the first artificial intelligence model which is trained using information on yields resulting from a plurality of synthesis methods as training data.

More specifically, the computing device 100 may generate a first artificial intelligence model which learns yield information of each synthesis method, and a first artificial intelligence model which does not learn the yield information of each synthesis method, and may use, by default, a process of drawing result values through the first artificial intelligence model which does not learn the yield information of each synthesis method to prioritize prediction of a synthetic material satisfying a specific condition. The computing device 100 may re-extract a synthesis method through the first artificial intelligence model which learns the yield information of each synthesis method only in the case of scaling up a synthetic material due to an approval for and completion of development of the synthetic material.

FIG. 17 is a flowchart illustrating a method of setting test conditions for a synthetic material through a second artificial intelligence model according to various embodiments.

Referring to FIG. 17, the computing device 100 may set a condition for a test of a specific synthetic material (e.g., a preclinical trial or clinical trial).

In step S810, the computing device 100 may generate and train a second artificial intelligence model.

Here, the structure and operations of the second artificial intelligence model may be the same as those of the first artificial intelligence model but are not limited thereto.

According to various embodiments, the computing device 100 may train the second artificial intelligence model using information on a plurality of synthetic materials and information on a test (e.g., a condition for performing a preclinical trial or clinical trial for the plurality of synthetic materials, test results under the set condition, etc.) as training data.

In step S820, the computing device 100 may acquire information on a synthetic material for which a preclinical trial or clinical trial will be performed.

In step S830, the computing device 100 may set a condition for testing the synthetic material using the information on the synthetic material acquired through step S820 as an input value for the second artificial intelligence model.

The second artificial intelligence model is a model which is trained using information on a plurality of synthetic materials and information on tests as training data, that is, a model trained with test results. Accordingly, it is possible to extract a test condition for drawing an optimal test result with a simple operation of inputting information on a specific synthetic material to the second artificial intelligence model.

In addition, since the second artificial intelligence model is a model which learns test results under a test condition for each synthetic material, it is possible to extract test result prediction values of a synthetic material as result values using a specific condition for a test of the synthetic material as an input value.

According to various embodiments, the computing device 100 may retrain the second artificial intelligence model using results of a test performed on a training material under a condition set according to the above method as training data.

FIG. 18 is a diagram illustrating a method of drawing information on patients and dosages suitable for a new drug through a third artificial intelligence model in the case of developing the new drug according to various embodiments.

Referring to FIG. 18, when development of a new drug is approved and completed with respect to a specific synthetic material through the operations of FIGS. 17 and 18, the computing device 100 may extract information on patients and dosages suitable for a new drug including the specific synthetic material in the case of developing the new drug.

In step S910, the computing device 100 may generate and train a third artificial intelligence model.

Here, the structure and operations of the third artificial intelligence model may be the same as those of the first and second artificial intelligence models but are not limited thereto.

According to various embodiments, the computing device 100 may train the third artificial intelligence model using, as training data, information on a plurality of test subjects, information on a plurality of synthetic materials developed as new materials, and test results of each of the plurality of synthetic materials developed as the new materials.

For example, the computing device 100 may train the third artificial intelligence model using, as training data, information on a plurality of patients, information on a plurality of synthetic materials developed as new drugs, and preclinical trial or clinical trial results of each of the plurality of synthetic materials developed as the new drugs.

In step S920, the computing device 100 may acquire information on a synthetic material of which a test is completed.

For example, the computing device 100 may acquire information on a synthetic material with which development of a new drug is approved and completed.

In step S930, the computing device 100 may extract, as result values, information on a subject and dosage suitable for using the new drug including the synthetic material using the information on the synthetic material acquired through step S920 as an input value for the third artificial intelligence model.

For example, information on a patient and dosage suitable for using the new drug including the synthetic material may be extracted as result values using the information on the synthetic material acquired through step S920 as an input value for the third artificial intelligence model.

In an embodiment related to new drug development, the third artificial intelligence model is a model trained using information on a plurality of patients, information on a plurality of synthetic materials developed as new drugs, and preclinical trial or clinical trial results of each of the plurality of synthetic materials developed as the new drugs as training data, that is, a model which learns correlation between attributes (ages, sexes, underlying diseases, etc.) of patients and new drug effects and correlation between dosage and new drug effects. Accordingly, it is possible to extract information on a suitable patient for the new drug and a proper amount of dosage with a simple operation of inputting information on a specific synthetic material to the third artificial intelligence model.

Also, the computing device 100 may not only directly guide the user through new drug development using artificial intelligence models as described above but also indirectly guide the user by providing documents which are helpful in a research field, matching the user to a researcher who studies in a similar field, etc.

More specifically, as shown in FIG. 19, the computing device 100 may extract important detailed conditions (a substance used as a material, equipment, a synthesis process, etc.) by analyzing standardized research record data pregenerated according to a specific user (researcher), and retrieve and provide non-standardized data (e.g., papers and patents) satisfying the extracted detailed conditions, thereby providing data optimized for research content.

Figure 20:
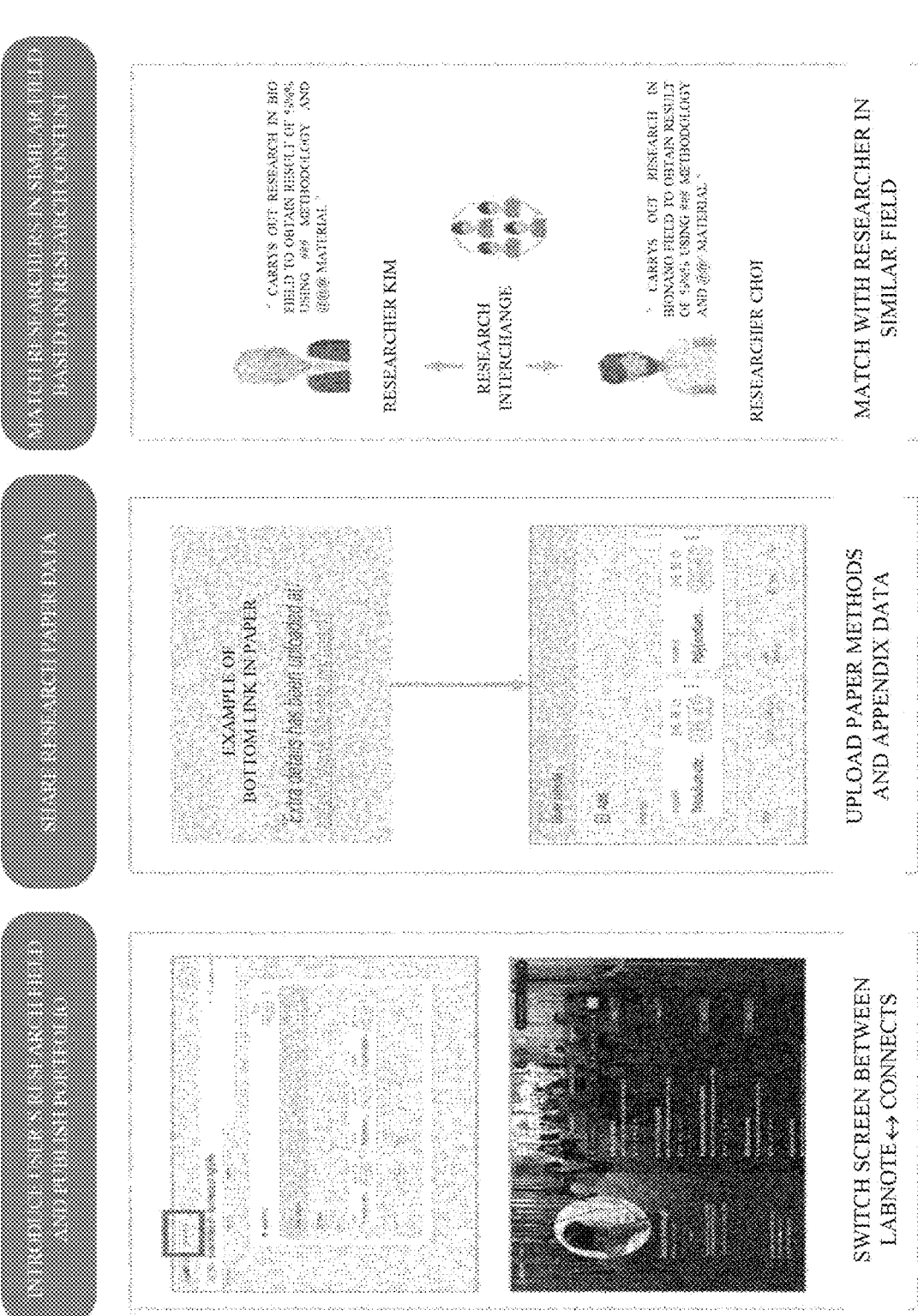
FIG. 20 is a diagram illustrating a process of recommending and matching a researcher on the basis of standardized research record data according to various embodiments.

Also, as shown in FIG. 20, the computing device 100 can provide a research sharing and cooperation platform that provides a function of publishing information (e.g., personal information, a research field, and a portfolio) on a specific user (researcher) or sharing research paper data and a function of matching a user to other researchers who study in similar fields on the basis of research content.

The method of automatically generating standardized research record data for training an artificial intelligence model and the method of providing a synthetic material development process using an artificial intelligence model have been described above with reference to flowcharts shown in the drawings. For simple description, the method of automatically generating standardized research record data for training an artificial intelligence model and the method of providing a synthetic material development process using an artificial intelligence model have been illustrated as series of blocks and described. However, the present invention is not limited to the order of blocks, and some blocks may be performed simultaneously or in a different order from that illustrated and described herein. Also, the methods can be performed with a new block which has not been described herein and has not been shown in drawings added or some blocks deleted or changed. The UI 10 provided by the computing device 100 will be described below with reference to FIGS. 21 to 24.

FIGS. 21 to 24 are diagrams illustrating forms of UIs applicable to various embodiments.

Referring to FIGS. 21 to 24, the UI 10 may include the first button 11 for inputting information on experiment materials, the second button 12 for inputting information on experimental equipment, and the third button 13 for inputting information on experiment and research processes.

In response to the user's selecting at least one of the first button 11, the second button 12, and the third button 13, the computing device 100 may provide a UI for receiving any one of information on an experimental material, information on experimental equipment, and information on an experiment and research process. For example, when the user selects (e.g., makes a mouse click on) the first button 11 on the UI 10, a UI 14 for inputting information on an experimental material may be provided as a popup window.

Although not shown in the drawings, the computing device 100 may likewise provide a UI for receiving information on experiment equipment in response to the user's selecting the second button 12 and provide a UI for receiving information on an experiment and research process in response to the user's selecting the third button 13. Like the UI 14 for inputting information on an experimental material, each UI may be output as a popup window.

The computing device 100 may generate experimental material information, research and experiment process information, and research result information by autocompleting and relating keywords of experimental materials, a research and experiment process, and research results input through the UI 14 for inputting information on an experimental material, the UI for inputting information on experimental equipment, and the UI for inputting information on an experiment and research process and may arrange and register on the UI 10 according to a preset template. For example, as shown in FIG. 23, information may be provided in individual boxes, and information belonging to the same category may be arranged in the same column.

Here, a card including specific information disposed (registered) on the UI 10 may be freely copied and disposed in another area on the UI 10 upon the user's request. For example, in response to a copy request (e.g., selecting a first card 16 and pressing a preset key (e.g., Ctrl)+dragging) for the first card 16 including information on a specific experimental material, the computing device 100 may generate, display, and register a second card 16' which is a copy of the first card 16 in an area designated by the user (e.g., an area in which a mouse pointer is present after the drag input).

Also, a plurality of cards including specific information arranged (registered) on the UI 10 may be freely mixed upon the user's request. For example, in response to a mix request (e.g., selecting and dragging a first card over a second card, selecting and dragging the second card over the first card, or the like) for the first card including information on a first experimental material and the second card including information on a second experimental material, the computing device 100 may generate a new third card (e.g., including information on the first experimental material and information on the second experimental material) by combining the information included in the first card and the information included in the second card together.

When all information is arranged (registered) on the UI 10 and standardized research record data is finally completed, the computing device 100 may provide summary information of the standardized research record information through a summary information provision UI 17.

Embodiments of the present invention have been described above with reference to the accompanying drawings, but those skilled in the technical field to which the present invention pertains can understand that the present invention can be implemented in other specific forms without changing technical spirit or essential features. Therefore, it should be understood that the embodiments described above are illustrative in all aspects and are not restrictive.

The invention claimed is:

1. A method of automatically generating standardized research record data for training an artificial intelligence model, the method being performed by a computing device and comprising:

receiving research record information of an experiment;

processing the received research record information on the basis of prestored experiment-related data; and generating standardized research record data using the processed research record information, wherein the received research record information includes a keyword relating to an experimental material, a keyword relating to a research and experiment process, and a keyword relating to research result information, and the processing of the received research record information comprises:

autocompleting a keyword relating to an experimental material and input by a user using prestored data related to experimental materials to generate experimental material information and synchronizing the generated experimental material information with the prestored data related to the experimental materials;

autocompleting a keyword relating to a research and experiment process and input by the user using prestored data related to research and experiment processes to generate research and experiment process information and synchronizing the generated research and experiment process information with the prestored data related to the research and experiment processes; and visualizing a keyword relating to a research result and input by the user on the basis of a preset result data format.

2. The method of claim 1, wherein the receiving of the research record information comprises:

receiving research record information in a form of prose including one or more text sentences; and analyzing the received research record information in the form of prose to extract a keyword relating to an experimental material, a keyword relating to a research and experiment process, and a keyword relating to a research result.

3. The method of claim 1, wherein the receiving of the research record information comprises:

providing a user interface (UI) for inputting the research record information; and receiving a keyword relating to an experimental material, a keyword relating to a research and experiment process, and a keyword relating to a research result through the UI.

4. The method of claim 1, wherein the receiving of the research record information comprises:

providing a user interface (UI) for inputting the research record information, receiving research record information in a form of voice through the UI, and performing a natural language processing (NLP) on the received research record information in the form of voice to extract a keyword relating to an experimental material, a keyword relating to a research and experiment process, and a keyword relating to a research result; and recognizing equipment usage information and material usage information through one or more sensors.

5. The method of claim 1, wherein the generating of the standardized research record data comprises:

simulating an experiment according to an experimental material, experimental equipment, and an experimental process included in first standardized research record data; and matching and storing results of simulating the experiment and the first standardized research record data.

6. The method of claim 1, further comprising:

training a first artificial intelligence model using the generated standard research record data as training data;

predicting a composition and structure of a material satisfying a condition input by a user using the trained first artificial intelligence model and drawing a method of synthesizing the material to have the predicted composition and structure; and providing result data including information on the predicted composition and structure of the material and information on the drawn method to the user.

7. The method of claim 6, wherein the training of the first artificial intelligence model comprises retraining the first artificial intelligence model using, as training data, an actual synthesis method for the material which is input by the user in response to the result data provided to the user, a comparison between a result of the actual synthesis method and a result of the drawn method, and properties of a material generated according to the actual synthesis method.

8. The method of claim 6, further comprising, in a case of scaling up a specific material drawn through the first artificial intelligence model, extracting information on a synthesis method and process optimized for the specific material through a second artificial intelligence model which is a model pretrained using synthesis methods each for a plurality of materials and information on yields resulting from the synthesis methods as training data.

9. A device for automatically generating standardized research record data for training an artificial intelligence model, the device comprising:

a processor;

a network interface;

a memory; and a computer program loaded into the memory and executed by the processor, wherein the computer program comprises:

an instruction to receive research record information of an experiment;

an instruction to process the received research record information on the basis of prestored experiment-related data; and an instruction to generate standardized research record data using the processed research record information, wherein the received research record information includes a keyword relating to an experimental material, a keyword relating to a research and experiment process, and a keyword relating to research result information, and the instruction to process the received research record information comprises:

an instruction to autocomplete a keyword relating to an experimental material and input by a user using prestored data related to experimental materials to generate experimental material information and synchronize the generated experimental material information with the prestored data related to the experimental materials;

an instruction to autocomplete a keyword relating to a research and experiment process and input by the user using prestored data related to research and experiment processes to generate research and experiment process information and synchronize the generated research and experiment process information with the prestored data related to the research and experiment processes; and an instruction to visualize a keyword relating to a research result and input by the user on the basis of a preset result data format.

10. A computer-readable recording medium on which a program for executing a method of automatically generating standardized research record data for training an artificial intelligence model in conjunction with a computing device is recorded, wherein the method comprises:

receiving research record information of an experiment;

processing the received research record information on the basis of prestored experiment-related data; and generating standardized research record data using the processed research record information, wherein the received research record information includes a keyword relating to an experimental material, a keyword relating to a research and experiment process, and a keyword relating to research result information, and the processing of the received research record information comprises:

autocompleting a keyword relating to an experimental material and input by a user using prestored data related to experimental materials to generate experimental material information and synchronizing the generated experimental material information with the prestored data related to the experimental materials;

autocompleting a keyword relating to a research and experiment process and input by the user using prestored data related to research and experiment processes to generate research and experiment process information and synchronizing the generated research and experiment process information with the prestored data related to the research and experiment processes; and visualizing a keyword relating to a research result and input by the user on the basis of a preset result data format.

* * * * *